United States Patent
Laitar et al.

(10) Patent No.: US 10,233,284 B2
(45) Date of Patent: *Mar. 19, 2019

(54) ALKYLENE OXIDE POLYMERIZATION USING A DOUBLE METAL CYANIDE CATALYST COMPLEX AND A MAGNESIUM, GROUP 3-GROUP 15 METAL OR LANTHANIDE SERIES METAL COMPOUND

(71) Applicant: Dow Global Technologies LLC, Midland, MI (US)

(72) Inventors: David S. Laitar, Midland, MI (US); David A. Babb, Lake Jackson, TX (US); Carlos M. Villa, Lake Jackson, TX (US); Richard Keaton, Pearland, TX (US); Jean-Paul Masy, Destelbergen (BE)

(73) Assignee: Dow Global Technologies LLC, Midland, MI (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/382,519

(22) Filed: Dec. 16, 2016

(65) Prior Publication Data

US 2017/0101506 A1    Apr. 13, 2017

Related U.S. Application Data

(63) Continuation of application No. 14/694,258, filed on Apr. 23, 2015, now Pat. No. 9,556,309, which is a continuation of application No. 13/990,697, filed as application No. PCT/US2011/065695 on Dec. 18, 2011, now Pat. No. 9,040,657.

(60) Provisional application No. 61/427,331, filed on Dec. 27, 2010.

(51) Int. Cl.
| | |
|---|---|
| *C08G 65/34* | (2006.01) |
| *C07C 41/02* | (2006.01) |
| *C07C 41/01* | (2006.01) |
| *C08G 65/26* | (2006.01) |

(52) U.S. Cl.
CPC .......... *C08G 65/2663* (2013.01); *C07C 41/01* (2013.01); *C07C 41/02* (2013.01); *C08G 65/269* (2013.01); *C08G 65/34* (2013.01)

(58) Field of Classification Search
CPC ..................................................... C08G 65/34
USPC ................................ 528/412, 408, 411, 416
See application file for complete search history.

(56) References Cited

U.S. PATENT DOCUMENTS

| | | | |
|---|---|---|---|
| 6,753,402 B1 | 6/2004 | Bauer | |
| 9,040,657 B2 * | 5/2015 | Laitar | ............... C08G 65/2663 528/408 |
| 9,556,309 B2 * | 1/2017 | Laitar | ................... C08G 65/34 |
| 2003/0119663 A1 | 6/2003 | Ooms | |
| 2008/0021191 A1 | 1/2008 | Reese | |
| 2013/0211041 A1 | 8/2013 | Kunst | |

FOREIGN PATENT DOCUMENTS

| | | |
|---|---|---|
| CA | 2790038 A | 8/2011 |
| DE | 19949091 A | 4/2001 |
| DE | 102010008410 A | 8/2011 |
| EP | 0090445 A | 5/1983 |
| WO | 2006/047436 A | 5/2006 |
| WO | 2011/137011 A | 11/2011 |
| WO | 2012/022048 A | 2/2012 |
| WO | 2012/091968 A | 7/2012 |

* cited by examiner

*Primary Examiner* — Duc Truong

(57) ABSTRACT

Alkylene oxide polymerizations are performed in the presence of a double metal cyanide polymerization catalyst and certain magnesium, Group 3-Group 15 metal or lanthanide series metal compounds. The presence of the magnesium, Group 3-Group 15 metal or lanthanide series metal compound provides several benefits including more rapid catalyst activation, faster polymerization rates and the reduction in the amount of ultra high molecular weight polymers that are formed. The catalyst mixture is unexpectedly useful in making polyethers having low equivalent weights.

15 Claims, No Drawings

ALKYLENE OXIDE POLYMERIZATION USING A DOUBLE METAL CYANIDE CATALYST COMPLEX AND A MAGNESIUM, GROUP 3-GROUP 15 METAL OR LANTHANIDE SERIES METAL COMPOUND

This application is a CON of Ser. No. 14/694,258 filed Apr. 23, 2015 now U.S. Pat. No. 9,556,309 Which is a CON of Ser. No. 13/990,697 filed May 30, 2013 now U.S. Pat. No. 9,040,657 Which is a 371 of PCT/2011/065695 FILED Dec. 18, 2011 WHICH CLAIMS BENEFIT OF 61/427,331 FILED Dec. 17, 2010.

This invention relates to a process for polymerizing an alkylene oxide in the presence of a double metal cyanide (DMC) polymerization catalyst.

Polyether monols and polyols are produced globally in large quantities. Polyether polyols are an important raw material for producing polyurethanes. Polyether monols are used, for example, as surfactants and industrial solvents, among other uses.

Polyether monols and polyols are produced by polymerizing an alkylene oxide in the presence of an initiator compound. The initiator compound has one or more functional groups at which the alkylene oxide can react to begin forming the polymer chains. The main functions of the initiator compound are to provide molecular weight control and to establish the number of hydroxyl groups that the polyether will have. The most widely used initiator compounds are low molecular weight hydroxyl-containing compounds, examples of which include, for example, glycerin, trimethylolpropane, ethylene glycol, diethylene glycol, propylene glycol, dipropylene glycol, pentaerythritol, sorbitol and sucrose.

A catalyst is needed to obtain economical polymerization rates. The most commonly used catalysts are alkali metal hydroxides such as potassium hydroxide and the so-called double metal cyanide (DMC) catalyst complexes, of which zinc hexacyanocobaltate catalyst complexes are the most commercially important type.

The DMC catalyst complexes have certain advantages over the alkali metal hydroxides. Polyethers produced using alkali metal hydroxide catalysts must be neutralized and purified to remove the catalyst residues. These steps add expense and create waste streams. One advantage of using the DMC catalyst complexes is that the catalyst residues often can be left in the product, unlike the case when alkali metal hydroxides are used as the polymerization catalyst. This can result in lower production costs. And whereas alkali metal hydroxide catalysts can promote a side reaction that forms unwanted monofunctional species, the DMC catalyst complexes tend to form polyether products that are nearly devoid of those species. Unlike alkali metal hydroxide catalysts, DMC catalyst complexes produce low polydispersity polymers when the polymerization is performed in a back-mixed continuous main reactor. These advantages create strong incentives to use DMC catalyst complexes in commercial-scale polymerization processes.

However, DMC catalysts have several problems that limit their use.

One problem with DMC complexes is that they sometimes activate slowly, or do not activate at all. The preparation of polyethers using the DMC catalyst typically begins with a stage of the reaction known as the catalyst induction period. During this stage of the reaction, the DMC catalyst is believed to become converted in situ from an inactive form into a highly active form that rapidly polymerizes the alkylene oxide as long as it remains active. This catalyst induction period is typically an indeterminate period of time following the first introduction of alkylene oxide to the reactor. It is common to introduce a small amount of alkylene oxide at the start of the polymerization process and then wait unit the catalyst has become activated (as indicated, for example, by a drop in reactor pressure due to the consumption of the initial alkylene oxide charge) before continuing with the alkylene oxide feed. Such a process is disclosed in U.S. Pat. No. 5,844,070. Very little or no polymerization occurs until the catalyst has become activated, so long activation times have a direct negative impact on the productivity of the process. It is sometimes the case that the catalyst does not become activated at all. Such a failure of the catalyst to activate typically will result in the abandonment of the attempt, and the process is started over again from the beginning. Therefore the activation process results in some loss of productivity under the best circumstances, and under the worst circumstances can cause a loss of the entire batch of starting mixture. The reduction or elimination of the induction period at the start of the alkoxylation reaction is therefore seen to be highly desirable.

A second problem has to do with the cost of the catalyst. Whereas alkali metal hydroxide polymerization catalysts are quite inexpensive, DMC catalyst complexes often cost hundreds of dollars per pound. Therefore, they have to be used in very small quantities so that catalyst costs do not become prohibitive. Catalyst concentrations below about 25 ppm (based on the weight of the polyether product) tend to be too small to provide an economical polymerization rate. It would be desirable if lower amounts of the expensive DMC catalyst complex could be used.

A third problem is that DMC catalyst complexes perform poorly in the presence of high concentrations of hydroxyl groups, and especially in the presence of initiator compounds like glycerin that have hydroxyl groups in the 1,2- or 1,3-positions with respect to each other. Under these conditions, the catalysts are difficult to activate, perform sluggishly and often become deactivated before the polymerization is completed. This represents a significant limitation on the widespread adoption of DMC catalysts.

For example, DMC catalysts are rarely if ever used commercially to produce polyols that have hydroxyl equivalent weights (molecular weight divided by the number of hydroxyl groups per molecule) below about 400, because the concentration of hydroxyl groups and initiator compounds is high enough during the polymerization process that the DMC catalyst does not perform well. This eliminates DMC catalyst complexes from being used to produce a class of polyether polyols that have hydroxyl equivalent weights ranging from about 85 to 400, and especially from 125 to 300. This class of polyether polyols is produced in large quantities for use in producing rigid polyurethane foams and for the preparation of coatings, adhesives, sealants, and elastomer polymers.

DMC catalyst complexes have been used commercially to produce higher equivalent weight polyols, but even then the problem of catalyst deactivation increases process complexity and expense, and much of the potential advantage of selecting DMC catalyst complexes instead of alkali metal hydroxide catalysts is not realized.

The alkoxylation of low hydroxyl equivalent weight initiators cannot proceed directly from the initiator compound to the finished polyol, because the high concentration of hydroxyl groups and initiator compound during early stages of the polymerization severely inhibits initial catalyst activation, and often results in failure of catalyst induction or in premature deactivation of the catalyst early in the alkoxylation process. This problem is avoided by performing the early stages of the polymerization in the presence of an alkali metal catalyst. This allows an alkoxylated intermediate having a hydroxyl equivalent weight of about 80 to 400 to be produced. This intermediate is recovered and the remainder of the polymerization is performed using the DMC catalyst. This approach requires the intermediate to be neutralized and purified to some extent (because the DMC catalyst is deactivated by strong bases), thus re-introducing costs which the DMC-catalyzed polymerization is intended to avoid. Even when an intermediate is used in this manner, it is sometimes necessary to perform the polymerization in the presence of a large amount of the higher equivalent weight final product. The presence of a large amount of product in the reaction mixture reduces the concentration of hydroxyl groups, and helps to ameliorate the problem of catalyst deactivation. Unfortunately, it reduces the amount of fresh product that can be prepared in a semi-batch reactor.

Solutions to the problem of catalyst deactivation in the presence of high concentration of hydroxyl groups have been proposed, but none has been found to be fully satisfactory, and none has led to the commercial-scale production of low hydroxyl equivalent weight polyether polyols. U.S. Pat. No. 6,077,978 attributes the problem, at least in part, to the presence of residual alkali in commercial-grade initiator compounds like glycerin, and describes adding small quantities of an acid to glycerin. US Published Patent Application No. 2008-021191 also describes adding phosphoric acid into the polymerization process; in this case the phosphoric acid is said to allow the polymerization to proceed from a low molecular weight starter in the presence of up to 5000 ppm of water. These approaches have not been entirely satisfactory, since the residual salts produced by the neutralization can still hinder the DMC catalyst. Long catalyst activation times are still commonly seen, together with sluggish reactions and rapid deactivation of the catalyst. These approaches also have not addressed the problem of producing low equivalent weight polyols using a DMC catalyst complex.

Another approach to improve the activity of DMC catalyst complexes is to add quaternary ammonium halides into the alkoxylation reaction. See Lee et al., Polymer 48 (2007) 4361-4367.

A fourth problem is that DMC catalyst complexes often produce a small amount of very high molecular weight (40,000+g/mol) polymers. The presence of these polymers increases polyol viscosity and can also adversely affect the ability of the polyether polyols made with DMC catalyst complexes to produce flexible polyurethane foam.

Certain metal alkoxides have been evaluated as alkylene oxide polymerization catalysts. See, e.g., Osgan et al., *J. Polym. Sci.* 34 (1959) 153-156; Miller et al., *J. Polym. Sci.*, 34 (1959) 161-163; Jedlinski et al., *Makromol. Chem.* 180, 949-952 (1979). Aluminum isopropoxide was reported to polymerize propylene oxide over a period of days, when used in large amounts (1% by weight, or 10,000 ppm) in a polymerization conducted at 80° C. The polymerization tended to stop short of completion, but the addition of zinc chloride was reported to allow the polymerization to proceed to completion, again using high (2% by weight) concentrations of the catalysts. Other metal alkoxides were reported as being even less effective catalysts.

Certain Lewis acids have been evaluated as alkylene oxide polymerization catalysts. The Lewis acids require essentially no activation time, but become deactivated rapidly and therefore cannot produce high molecular weight polymers or high conversions of alkylene oxide to polymer. In addition, poly(propylene oxide) polymers produced by Lewis acid catalysis tend to have approximately 50% secondary hydroxyls and 50% primary hydroxyls.

Metal halides such as zinc chloride and aluminum trichloride have been added into DMC alkoxylation reactions in an attempt to eliminate the formation of a high molecular weight "tail" material that is often seen in those polymerizations. See, e.g., U.S. Pat. No. 6,028,230. However, the data in that patent suggests that these metal halides provide no benefit in the absence of some small amount of water. Furthermore, only very small amounts of the metal halide can be tolerated. U.S. Pat. No. 6,028,230 reports that the DMC catalyst complex does not activate in the presence of 30 ppm of zinc chloride (0.007 moles of zinc/gram of DMC catalyst) in the absence of water, or in the presence of as little as 10 ppm (0.0024 moles of zinc/gram of DMC catalyst complex) when as little as 50 ppm of water is present.

There remains a desire to provide a viable process by which low hydroxyl equivalent weight polyols can be prepared using a DMC catalyst complex, as well as a desire to provide a more effective process by which polyols can be prepared by polymerizing an alkylene oxide in the presence of high concentrations of low equivalent weight initiators using a DMC catalyst complex.

There is also a desire to reduce the amount of DMC catalyst complex that is needed to obtain fast polymerization rates at commercial scales.

There is also a desire to provide a way of reducing activation time of a DMC catalyst complex.

In addition, there is a desire to reduce the high molecular weight "tail" that is associated with DMC-catalyzed alkylene oxide polymerizations.

This invention is in one aspect a method for producing a polyether monol or polyether polyol product, comprising polymerizing at least one alkylene oxide in the presence of a double metal cyanide catalyst complex and a magnesium Group 3-Group 15 metal or lanthanide series compound in which a magnesium, Group 3-Group 15 metal or lanthanide series metal is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, Group 3-Group 15 or lanthanide series metal compound is devoid of halide anions.

In a particular aspect, the invention is a method for producing a polyether monol or polyether polyol product, comprising (1) forming a catalyst mixture by combining (a) a double metal cyanide catalyst complex and (b) a magnesium, Group 3-Group 15 metal or lanthanide series metal compound in which a magnesium, Group 3-Group 15 metal or lanthanide series metal compound is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, Group 3-Group 15 metal or lanthanide series metal compound is devoid of halide anions, (2) combining the catalyst mixture with at least one alkylene oxide and then (3) polymerizing the alkylene oxide.

The invention is also an alkylene oxide polymerization catalyst mixture comprising a double metal cyanide catalyst complex and a magnesium, Group 3-Group 15 metal or lanthanide series metal compound in which a magnesium, Group 3-Group 15 metal or lanthanide series metal is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, Group 3-Group 15 metal or lanthanide series compound is devoid of halide anions.

The invention is also a method for producing an alkylene oxide polymerization catalyst mixture, comprising combining (a) a double metal cyanide catalyst complex and (b) a magnesium, Group 3-Group 15 metal or lanthanide series metal compound in which a magnesium, Group 3-Group 15 metal or lanthanide series metal is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, Group 3-Group 15 metal compound or lanthanide series metal is devoid of halide anions.

The method of the invention offers several advantages.

In some embodiments of the invention, the presence of the magnesium, Group 3-Group 15 metal or lanthanide series metal compound (sometimes referred to herein as "MG3-15LA compound") has been found to significantly reduce the time required to activate the double metal cyanide catalyst complex, compared to when the DMC catalyst complex is used by itself (i.e., when the MG3-15LA compound is absent). As discussed more fully below, the faster activation times in some cases correlate to the selection of the anion portion of the MG3-15LA compound. After the DMC catalyst complex has become activated, faster polymerization rates often are seen, compared to when the DMC catalyst complex is used by itself (i.e., when the MG3-15LA compound is absent). As discussed more fully below, certain metals appear to provide especially fast polymerization rates.

Very low concentrations of the DMC catalyst complex (well less than 25 ppm of the DMC catalyst complex, based on the weight of the product) have in many cases been found to provide commercially acceptable polymerization rates, particularly when the polyether product has a hydroxyl equivalent weight of 800 or more. The ability to perform the polymerization using very low catalyst levels can lead to a very significant reduction in catalyst costs.

In addition, the DMC catalyst performs well even when the concentration of hydroxyl groups is high during the polymerization process, activating rapidly and providing good polymerization rates without deactivating prematurely. Accordingly, the process is amenable to the production of polyether polyols that have hydroxyl equivalent weights in the range of from 85 to 400 (especially from 125 to 300), as well as to the production of polyether polyols having hydroxyl equivalent weights of from 401 to 5,000 or more. In addition, the process provides a method by which an alkylene oxide can be polymerized onto a low equivalent weight initiator compound such as glycerin or sorbitol.

The process of the invention is very well adapted for continuous polymerizations in which the initiator compound and the alkylene oxide are continuously added to the polymerization. It also is suitable for batch or semi-batch polymerization processes.

Yet another advantage is that the process of this invention tends to produce polyether polyol products that have very small levels of ultra-high molecular weight (40,000+g/mol) materials.

Suitable double metal cyanide catalysts include those described, for example, in U.S. Pat. Nos. 3,278,457, 3,278,458, 3,278,459, 3,404,109, 3,427,256, 3,427,334, 3,427,335 and 5,470,813. Some suitable DMC catalysts can be represented by the formula

wherein M and $M^3$ are each metals; $M^1$ is a transition metal different from M, each X represents a group other than cyanide that coordinates with the $M^1$ ion; $M^2$ is a transition metal; A represents an anion; b, c and d are numbers that reflect an electrostatically neutral complex; r is from 4 to 6; t is from 0 to 2; x and y are integers that balance the charges in the metal salt $M^3{}_xA_y$, and n is zero or a positive integer. The foregoing formula does not reflect the presence of neutral complexing agents such as t-butanol which are often present in the DMC catalyst complex.

M and $M^3$ each are preferably a metal ion independently selected from the group consisting of $Zn^{2+}$, $Fe^{2+}$, $Co^{+2+}$, $Ni^{2+}$, $Mo^{4+}$, $Mo^{6+}$, $Al^{+3+}$, $V^{4+}$, $V^{5+}$, $Sr^{2+}$, $W^{4+}$, $W^{6+}$, $Mn^{2+}$, $Sn^{2+}$, $Sn^{4+}$, $Pb^{2+}$, $Cu^{2+}$, $La^{3+}$ and $Cr^{3+}$, with $Zn^{2+}$ being preferred.

$M^1$ and $M^2$ are preferably $Fe^{3+}$, $Fe^{2+}$, $Co^{3+}$, $Co^{2+}$, $Cr^{2+}$, $Cr^{3+}$, $Mn^{2+}$, $Mn^{3+}$, $Ir^{3+}$, $Ni^{2+}$, $Rh^{3+}$, $Ru^{2+}$, $V^{4+}$, $V^{5+}$, $Ni^{2+}$, $Pd^{2+}$, and $Pt^{2+}$. Among the foregoing, those in the plus-three oxidation state are more preferred as the $M^1$ and $M^2$ metal. $Co^{+3}$ and $Fe^{+3}$ are even more preferred and $Co^{+3}$ is most preferred.

Suitable anions A include but are not limited to halides such as chloride, bromide and iodide, nitrate, sulfate, carbonate, cyanide, oxalate, thiocyanate, isocyanate, perchlorate, isothiocyanate, an alkanesulfonate such as methanesulfonate, an arylenesulfonate such as p-toluenesulfonate, trifluoromethanesulfonate (triflate) and a $C_{1-4}$ carboxylate. Chloride ion is especially preferred.

r is preferably 4, 5 or 6, preferably 4 or 6, and most preferably 6; t is preferably 0 or 1, most preferably 0. In most cases, r+t will equal six.

A suitable type of DMC catalyst is a zinc hexacyanocobaltate catalyst complex as described, for example, in any of U.S. Pat. Nos. 3,278,457, 3,278,458, 3,278,459, 3,404,109, 3,427,256, 3,427,334, 3,427,335 and 5,470,813. An especially preferred type of DMC catalyst is complexed with t-butanol.

The MG3-15LA compound is a separately added ingredient, which is not present during the preparation (i.e., the precipitation step) of the DMC catalyst complex. The mechanism by which the MG3-15LA compound provides benefits to the polymerization is not fully understood. Although the invention is not bound by any theory, it is possible that some reaction or other interaction between this compound and the DMC catalyst complex takes place.

The MG3-15LA compound contains a magnesium, Group 3-Group 15 metal or lanthanide series metal ion bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion. The MG3-15LA compound is devoid of halide anions.

By "alkoxide ion" it is meant a species having the form $^-$O—R, where R is an alkyl group or substituted alkyl group, and which is the conjugate base, after removal of a hydroxyl hydrogen, of an alcohol compound having the form HO—R. These alcohols typically have pKa values in the range of 13 to 25 or greater. The alkoxide ion in some embodiments may contain from one to 20, more preferably from one to 6 and still more preferably from 2 to 6 carbon atoms. The alkyl group or substituted alkyl group may be linear, branched and/or cyclic. Examples of suitable substituents include, for example, additional hydroxyl groups (which may be in the alkoxide form), ether groups, carbonyl groups, ester groups, urethane groups, carbonate groups, silyl groups, aromatic groups such as phenyl and alkyl-substituted phenyl, halogen, and the like. Examples of such alkoxide ions include methoxide, ethoxide, isopropoxide, n-propoxide, n-butoxide, sec-butoxide, t-butoxide, benzyloxy, and the like. In other embodiments, the R group may contain one or more hydroxyl groups and/or may contain one or more ether linkages. An alkoxide ion may correspond to the residue (after removal of one or more hydroxyl hydrogens) of an initiator compound that is present in the polymerization, such as those initiator compounds described below. The alkoxide ion may be an alkoxide formed by removing one or more hydroxyl hydrogens from a polyether monol or polyether polyol; such an alkoxide in some embodiments corresponds to a residue, after removal of one or more hydroxyl hydrogen atoms, of the polyether monol or polyether polyol product that is obtained from the alkoxylation reaction, or of a polyether having a molecular weight intermediate to that of the initiator compound and the product of the alkoxylation reaction.

By "aryloxy anion" it is meant a species having the form $^-$O—Ar, where Ar is an aromatic group or substituted group, and which corresponds, after removal of a hydroxyl hydrogen, to a phenolic compound having the form HO—Ar. These phenolic compounds may have a pKa of, for example, from about 9 to about 12. Examples of such aryloxy anions include phenoxide and ring-substituted phenoxides, wherein the ring-substituents include, for example, alkyl, $CF_3$, cyano, $COCH_3$, halogen, hydroxyl, alkoxyl and the like. The ring-substituent(s), if present, may be in one or more of the ortho-, para- and/or meta-positions relative to the phenolic group. The phenoxide anions also include the conjugate bases of polyphenolic compounds such as bisphenol A, bisphenol F and various other bisphenols, 1,1,1-tris(hydroxyphenyl)ethane, and fused ring aromatics such as 1-naphthol and the like.

A carboxylate anion preferably contains from one to 24, more preferably from 2 to 18 and still more preferably from 2 to 12 carbon atoms. It may be aliphatic or aromatic. An aliphatic carboxylic acid may contain substituent groups such as hydroxyl groups (which may be in the alkoxide form), ether groups, carbonyl groups, ester groups, urethane groups, carbonate groups, silyl groups, aromatic groups such as phenyl and alkyl-substituted phenyl, halogen, and the like. Examples of aliphatic carboxylate anions include formate, acetate, propionate, butyrate, 2-ethylhexanoate, n-octoate, decanoate, laurate and other alkanoates and halogen-substituted alkanoates such as 2,2,2-trifluoroacetate, 2-fluoroacetate, 2,2-difluoroacetate, 2-chloroacetate, 2,2,2-trichloroacetate and the like. Aromatic carboxylates include benzoate, alkyl-substituted benzoate, halo-substituted benzoate, 4-cyanobenzoate, 4-trifluoromethylbenzoate, salicylate, 3,5-di-t-butylsalicylate, subsalicylate, and the like. In some embodiments, such a carboxylate ion may be the conjugate base of a carboxylic acid having a pKa from 1 to 6, preferably from 3 to 5.

By "acyl anion", it is meant a conjugate base of a compound containing a carbonyl group including, for example, an aldehyde, ketone, carbonate, ester or similar compound that has an enol form. Among these are β-diketo compounds, such as acetoacetonate, butylacetoacetonate and the like.

Phosphate ester anions include those having the formula $^-$O—P(O)(OR$^1$)$_2$, wherein R is alkyl, substituted alkyl, phenyl or substituted phenyl. Thiophosphate esters have the corresponding structure in which one or more of the oxygens are replaced with sulfur.

By "amide anion", it is meant an ion in which a nitrogen atom bears a negative charge. The amide ion generally takes the form $^-$N(R$^2$)$_2$, wherein the R$^2$ groups are independently hydrogen, alkyl, aryl, trialkylsilyl, triarylsilyl and the like. The alkyl groups may be linear, branched or cyclic. Any of these groups may contain substituents such as ether or hydroxyl. The two R$^2$ groups may together form a ring structure, which ring structure may be unsaturated and/or contain one or more heteroatoms (in addition to the amide nitrogen) in the ring.

Hydrocarbyl anions include aliphatic, cycloaliphatic and/or aromatic anions wherein the negative charge resides on a carbon atom. The hydrocarbyl anions are conjugate bases of hydrocarbons that typically have pKa values in excess of 30. The hydrocarbyl anions may also contain inert substituents. Of the aromatic hydrocarbyl anions, phenyl groups and substituted phenyl groups are preferred. Aliphatic hydrocarbyl anions are preferably alkyl groups, which more preferably contain from 1 to 12, more preferably from 2 to 8 carbon atoms. Methyl, ethyl, n-propyl, isopropyl, n-butyl, sec-butyl, isobutyl, cyclopentadienyl and t-butyl anions are all useful, for example.

Preferred anions are the conjugate base of a compound having a pKa of at least 1.5, preferably at least 2.5, still more preferably at least 3.0. The pKa of the conjugate acid has been found to relate to the time required to activate the DMC catalyst complex in a polymerization process of this invention. It has been found that shorter activation times are generally seen when the anions correspond to the conjugate base of a compound having a pKa of at least 9, preferably at least 12, more preferably at least 13. The anion may be the conjugate base of a compound having any higher pKa, such as up to 60 or higher. Anions corresponding to the conjugate base of a compound having a pKa of less than 9, especially less than 5, often have been found to lead to longer activation times. Therefore, especially preferred anions are alkoxide, aryloxy, amide, and hydrocarbyl anions which are the conjugate base of a compound having a pKa of at least 9, more preferably at least 12 and still more preferably at least 13, up to 60 or greater.

The Group 3-Group 15 metals are metals falling within any of groups III through 15, inclusive, of the 2010 IUPAC periodic table of the elements. The metal may be, for example, scandium, yttrium, lanthanum, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, mercury, aluminum, gallium, indium, tellurium, germanium, tin, lead, antimony, bismuth, and the lanthanide series metals including those having atomic numbers from 58 (cerium) to 71 (lutetium), inclusive.

Preferred metals include those in Groups 3, 4, 5, 12, 13 and 14. Among these, scandium, yttrium, hafnium, titanium, zirconium, niobium, vanadium, zinc, aluminum, gallium, indium and tin are more preferred, as these metals tend to provide fast polymerization rates and/or allow very small quantities of the DMC catalyst to be present. Aluminum, zinc, hafnium, gallium, indium, tin, titanium and zirconium are especially preferred.

Among the suitable MG3-15LA compounds are those corresponding to either of the formula $M^4A^1_z$ and $M^4(O)A^1_z$, wherein $M^4$ is the magnesium, Group 3-Group 15 or lanthanide series metal and each $A^1$ is independently an anion as described before and z is a number of at least one which reflects an electrostatically neutral compound, provided that any two or more $A^1$ groups may together form a polyvalent group. Each $A^1$ preferably is independently an alkoxide, aryloxy anion, amide anion or hydrocarbyl anion that is the conjugate base of a compound having a pKa of at least 9, more preferably at least 12 and still more preferably at least 13. As before, any $A^1$ may be an alkoxide anion which is the conjugate base of an initiator compound or a polyether monol or polyether polyol, including the polyether monol or polyether polyol product that is obtained from the alkoxylation reaction or a polyether having a molecular weight intermediate to that of the initiator compound and the product of the alkoxylation reaction.

The MG3-15LA compound is preferably devoid of anions that are conjugate bases of inorganic acids such as sulfate, sulfite, persulfate, nitrate, nitrite, chlorate, perchlorate, hypochlorite, carbonate, chromate, and the like; sulfonate anions such as trifluoromethylsulfonate and methyl sulfonate; and hydroxide ions.

Examples of suitable MG3-15LA compounds include but are not limited to:

a) magnesium alkyls such as diethyl magnesium, dibutyl magnesium, butylethyl magnesium, dibenzyl magnesium and the like; magnesium alkoxides such as magnesium methoxide, magnesium ethoxide, magnesium isopropoxide, magnesium t-butoxide, magnesium sec-butoxide and the like; magnesium aryloxides such as magnesium phenoxide, and magnesium phenoxides in which one or more of the phenoxide groups is ring-substituted with alkyl, $CF_3$, cyano, $COCH_3$, halogen, hydroxyl, alkoxyl and the like; magnesium carboxylates such as magnesium formate, magnesium acetate, magnesium propionate, magnesium 2-ethylhexanoate, magnesium benzoate, magnesium benzoates in which one or more of the benzoate groups is ring-substituted with alkyl, $CF_3$, cyano, $COCH_3$, halogen, hydroxyl, alkoxyl and the like, magnesium salicylate, magnesium 3,5-di-t-butyl salicylate; magnesium amides such as magnesium dimethylamide, magnesium diethylamide, magnesium diphenylamide, magnesium bis(trimethylsilyl)amide and the like; magnesium acetylacetonate and magnesium t-butylacetylacetonate.

b) scandium alkoxides such as scandium methoxide, scandium ethoxide, scandium isopropoxide, scandium t-butoxide, scandium sec-butoxide and the like; scandium aryloxides such as scandium phenoxide and scandium phenoxides in which one or more of the phenoxide groups is ring-substituted with alkyl, $CF_3$, cyano, $COCH_3$, halogen, hydroxyl, alkoxyl and the like; scandium carboxylates such as scandium formate, scandium acetate, scandium propionate, scandium 2-ethylhexanoate, scandium benzoate, scandium benzoates in which one or more of the benzoate groups is ring-substituted with alkyl, $CF_3$, cyano, $COCH_3$, halogen, hydroxyl, alkoxyl and the like; scandium salicylate; scandium acetylacetonate and scandium t-butylacetylacetonate.

c) yttrium alkoxides such as yttrium methoxide, yttrium ethoxide, yttrium isopropoxide, yttrium t-butoxide, yttrium sec-butoxide and the like; yttrium aryloxides such as yttrium phenoxide, and yttrium phenoxides in which one or more of the phenoxide groups is ring-substituted with alkyl, $CF_3$, cyano, $COCH_3$, halogen, hydroxyl, alkoxyl and the like; yttrium carboxylates such as yttrium formate, yttrium acetate, yttrium propionate, yttrium 2-ethylhexanoate, yttrium benzoate, yttrium benzoates in which one or more of the benzoate groups is ring-substituted with alkyl, $CF_3$, cyano, $COCH_3$, halogen, hydroxyl, alkoxyl and the like, yttrium salicylate, yttrium 3,5-di-t-butyl salicylate; yttrium amides such as yttrium dimethylamide, yttrium diethylamide, yttrium diphenylamide, yttrium bis(trimethylsilyl)amide and the like; yttrium acetylacetonate and yttrium t-butylacetylacetonate.

d) hafnium alkyls such as such as tetraethyl hafnium, tetrabutyl hafnium, tetrabenzyl hafnium and the like; hafnium alkoxides such as hafnium tetramethoxide, hafnium tetraethoxide, hafnium tetraisopropoxide, hafnium tetra-t-butoxide, hafnium tetra-sec-butoxide and the like; hafnium aryloxides such as hafnium phenoxide and hafnium phenoxides in which one or more of the phenoxide groups is ring-substituted with alkyl, $CF_3$, cyano, $COCH_3$, halogen, hydroxyl, alkoxyl and the like; hafnium carboxylates such as hafnium formate, hafnium acetate, hafnium propionate, hafnium 2-ethylhexanoate, hafnium benzoate, hafnium benzoates in which one or more of the benzoate groups is ring-substituted with alkyl, $CF_3$, cyano, $COCH_3$, halogen, hydroxyl, alkoxyl and the like, hafnium salicylate, hafnium 3,5-di-t-butyl salicylate; hafnium amides such as hafnium tetra(dimethylamide), hafnium tetra(diethylamide), hafnium tetra(diphenylamide), hafnium tetra((bistrimethylsilyl)amide); hafnium acetylacetonate and hafnium t-butylacetylacetonate;

e) titanium alkyls such as such as tetraethyl titanium, tetrabenzyl titanium and the like; titanium alkoxides such as titanium tetramethoxide, titanium tetraethoxide, titanium tetraisopropoxide, titanium tetra-t-butoxide, titanium tetra-sec-butoxide and the like; titanium aryloxides such as titanium phenoxide and titanium phenoxides in which one or more of the phenoxide groups is ring-substituted with alkyl, $CF_3$, cyano, $COCH_3$, halogen, hydroxyl, alkoxyl and the like; titanium carboxylates such as titanium formate, titanium acetate, titanium propionate, titanium 2-ethylhexanoate, titanium benzoate, titanium benzoates in which one or more of the benzoate groups is ring-substituted with alkyl, $CF_3$, cyano, $COCH_3$, halogen, hydroxyl, alkoxyl and the like, titanium salicylate, titanium 3,5-di-t-butyl salicylate; titanium amides such as titanium tetra(dimethylamide), titanium tetra(diethylamide, titanium tetra(diphenylamide), titanium tetra((bistrimethylsilyl)amide); titanium acetylacetonate and titanium t-butylacetylacetonate;

f) zirconium alkyls such as such as tetraethyl zirconium, tetrabutyl zirconium, tetrabenzyl zirconium and the like; zirconium alkoxides such as zirconium tetramethoxide, zirconium tetraethoxide, zirconium tetraisopropoxide, zirconium tetra-t-butoxide, zirconium tetra-sec-butoxide and the like; zirconium aryloxides such as zirconium phenoxide and zirconium phenoxides in which one or more of the phenoxide groups is ring-substituted with alkyl, $CF_3$, cyano, $COCH_3$, halogen, hydroxyl, alkoxyl and the like; zirconium carboxylates such as zirconium formate, zirconium acetate, zirconium propionate, zirconium 2-ethylhexanoate, zirconium benzoate, zirconium benzoates in which one or more of the benzoate groups is ring-substituted with alkyl, $CF_3$, cyano, $COCH_3$, halogen, hydroxyl, alkoxyl and the like, zirconium salicylate, zirconium 3,5-di-t-butyl salicylate; zirconium amides such as zirconium tetra(dimethylamide), zirconium tetra(diethylamide, zirconium tetra(diphenylamide), zirconium tetra((bistrimethylsilyl)amide); zirconium acetylacetonate and zirconium t-butylacetylacetonate;

g) vanadium alkoxides such as vanadium methoxide, vanadium ethoxide, vanadium isopropoxide, vanadium t-butoxide, vanadium sec-butoxide and the like; vanadium oxo tris(alkoxides) such as vanadium oxo tris(methoxide), vanadium oxo tris(ethoxide), vanadium oxo tris(isopropoxide), vanadium oxo tris(t-butoxide), vanadium oxo tris(sec-butoxide) and the like; vanadium aryloxides such as vanadium phenoxide and vanadium phenoxides in which one or more of the phenoxide groups is ring-substituted with alkyl, $CF_3$, cyano, $COCH_3$, halogen, hydroxyl, alkoxyl and the like; vanadium carboxylates such as vanadium formate, vanadium acetate, vanadium propionate, vanadium 2-ethylhexanoate, vanadium benzoate, vanadium benzoates in which one or more of the benzoate groups is ring-substituted with alkyl, $CF_3$, cyano, $COCH_3$, halogen, hydroxyl, alkoxyl and the like, vanadium salicylate, vanadium 3,5-di-t-butyl salicylate; vanadium tris(acetylacetonate) and vanadium tris (t-butylacetylacetonate); vanadium oxo bis(acetylacetonate);

h) zinc alkyls such as such as dimethyl zinc, diethyl zinc, dibutyl zinc, dibenzyl zinc and the like; alkyl zinc alkoxides such as ethyl zinc isopropoxide; zinc alkoxides such as zinc methoxide, zinc ethoxide, zinc isopropoxide, zinc t-butoxide, zinc sec-butoxide and the like; zinc aryloxides such as zinc phenoxide and zinc phenoxides in which one or more of the phenoxide groups is ring-substituted with alkyl, $CF_3$, cyano, $COCH_3$, halogen, hydroxyl, alkoxyl and the like; zinc carboxylates such as zinc formate, zinc acetate, zinc propionate, zinc 2-ethylhexanoate, zinc benzoate, zinc benzoates in which one or more of the benzoate groups is ring-substituted with alkyl, $CF_3$, cyano, $COCH_3$, halogen, hydroxyl, alkoxyl and the like, zinc salicylate, zinc 3,5-di-t-butyl salicylate; zinc amides such as zinc dimethylamide, zinc diethylamide, zinc diphenylamide, zinc (bistrimethylsilyl)amide; zinc acetylacetonate and zinc t-butylacetylacetonate;

i) trialkyl aluminum compounds such as trimethylaluminum, triethyl aluminum, tributyl aluminum, tribenzylaluminum and the like; aluminum alkoxides such as aluminum trimethoxide, aluminum triethoxide, aluminum triisopropoxide, aluminum tri-t-butoxide, aluminum tri-sec-butoxide and the like; aluminum aryloxides such as aluminum phenoxide and aluminum phenoxides in which one or more of the phenoxide groups is ring-substituted with alkyl, $CF_3$, cyano, $COCH_3$, halogen, hydroxyl, alkoxyl and the like; aluminum carboxylates such as aluminum formate, aluminum acetate, aluminum propionate, aluminum 2-ethylhexanoate, aluminum benzoate, aluminum benzoates in which one or more of the benzoate groups is ring-substituted with alkyl, $CF_3$, cyano, $COCH_3$, halogen, hydroxyl, alkoxyl and the like, aluminum salicylate, aluminum 3,5-di-t-butyl salicylate; aluminum amides such as aluminum tris(dimethylamide), aluminum tris(diethylamide), aluminum tris(diphenylamide), aluminum tris(di(trimethylsilyl)amide) and the like; aluminum acetylacetonate; aluminum t-butylacetylacetonate; and alkylaluminum oxides and alkoxides such as diethylaluminum ethoxide, dimethylaluminum ethoxide, diethylaluminum isopropoxide, dimethylaluminum isopropoxide, methyl aluminoxane, tetraethyldialuminoxane and the like;

j) trialkyl gallium compounds such as trimethylgallium, triethyl gallium, tributyl gallium, tribenzylgallium and the like; gallium alkoxides such as gallium trimethoxide, gallium triethoxide, gallium triisopropoxide, gallium tri-t-butoxide, gallium tri-sec-butoxide and the like; gallium aryloxides such as gallium phenoxide and gallium phenoxides in which one or more of the phenoxide groups is ring-substituted with alkyl, $CF_3$, cyano, $COCH_3$, halogen, hydroxyl, alkoxyl and the like; gallium carboxylates such as gallium formate, gallium acetate, gallium propionate, gallium 2-ethylhexanoate, gallium benzoate, gallium benzoates in which one or more of the benzoate groups is ring-substituted with alkyl, $CF_3$, cyano, $COCH_3$, halogen, hydroxyl, alkoxyl and the like, gallium salicylate, gallium 3,5-di-t-butyl salicylate; gallium amides such as gallium tris(dimethylamide), gallium tris(diethylamide), gallium tris (diphenylamide), gallium tris(di(trimethylsilyl)amide) and the like; gallium acetylacetonate; gallium t-butylacetylacetonate; and alkylgallium alkoxides such as diethylgallium ethoxide, dimethylgallium ethoxide, diethylgallium isopropoxide and dimethylgallium isopropoxide;

k) trialkyl indium compounds like trimethyl indium; indium alkoxides such as indium methoxide, indium ethoxide, indium isopropoxide, indium t-butoxide, indium sec-butoxide and the like; indium aryloxides such as indium phenoxide and indium phenoxides in which one or more of the phenoxide groups is ring-substituted with alkyl, $CF_3$, cyano, $COCH_3$, halogen, hydroxyl, alkoxyl and the like; indium carboxylates such as indium formate, indium acetate, indium propionate, indium 2-ethylhexanoate, indium benzoate, indium benzoates in which one or more of the benzoate groups is ring-substituted with alkyl, $CF_3$, cyano, $COCH_3$, halogen, hydroxyl, alkoxyl and the like, indium salicylate, indium 3,5-di-t-butyl salicylate; indium acetylacetonate; and indium t-butylacetylacetonate; and l) stannous phosphate; stannous pyrophosphate, stannous alkoxides such as stannous methoxide, stannous ethoxide, stannous isopropoxide, stannous t-butoxide, stannous sec-butoxide and the like; stannous aryloxides such as stannous phenoxide and stannous phenoxides in which one or more of the phenoxide groups is ring-substituted with alkyl, $CF_3$, cyano, $COCH_3$, halogen, hydroxyl, alkoxyl and the like; stannous carboxylates such as stannous formate, stannous acetate, stannous propionate, stannous 2-ethylhexanoate, stannous benzoate, stannous benzoates in which one or more of the benzoate groups is ring-substituted with alkyl, $CF_3$, cyano, $COCH_3$, halogen, hydroxyl, alkoxyl and the like, stannous salicylate, stannous 3,5-di-t-butyl salicylate; stannous acetylacetonate; and stannous t-butylacetylacetonate.

In addition to the foregoing, other suitable MG3-15LA compounds include magnesium, Group 3-Group 15 or lanthanide series metal alkoxides wherein one or more of the alkoxide group(s) are the conjugate base, after removal of one or more hydroxyl hydrogen atoms, from (1) an initiator compound as described below, (2) a polyether monol or polyether polyol product of the polymerization reaction or (3) a polyether having a molecular weight intermediate to the initiator and the polyether monol or polyether polyol product of the polymerization.

If desired, mixtures of two or more of the foregoing MG3-15LA compounds may be used.

The alkylene oxide may be, for example, ethylene oxide, 1,2-propylene oxide, 2,3-propylene oxide, 1,2-butane oxide, 2-methyl-1,2-butaneoxide, 2,3-butane oxide, tetrahydrofuran, epichlorohydrin, hexane oxide, styrene oxide, divinylbenzene dioxide, a glycidyl ether such as Bisphenol A diglycidyl ether, or other polymerizable oxirane. The preferred alkylene oxide by far is 1,2-propylene oxide, or a mixture of at least 50% (preferably at least 80%) by weight propylene oxide and up to 50% (preferably up to 20%) ethylene oxide.

The polymerization is preferably performed in the presence of a hydroxyl-containing initiator compound. The hydroxyl-containing initiator compound is any organic compound that is to be alkoxylated in the polymerization reaction. It contains 1 or more hydroxyl groups, preferably 2 or more hydroxyl groups. It may contain as many as 12 or more hydroxyl groups. Preferred initiators for producing polyols for use in polyurethane applications will have from 2 to 8 hydroxyl groups per molecule. In some embodiments, the initiator compound will have from 2 to 4 or from 2 to 3 hydroxyl groups. In other embodiments, the initiator compound will have from 4 to 8 or from 4 to 6 hydroxyl groups. The initiator compound may have at least two hydroxyl groups that are in the 1,2- or 1,3-positions with respect to each other (taking the carbon atom to which one of the hydroxyl groups is bonded as the "1" position). Mixtures of initiator compounds can be used.

The initiator compound will have a hydroxyl equivalent weight less than that of the polyether product. It may have a hydroxyl equivalent weight of from 30 to 500 or more. In some embodiments, the initiator compound has a hydroxyl equivalent weight of from 30 to 125, especially from 30 to 100.

Suitable initiators include but are not limited to ethylene glycol, diethylene glycol, triethylene glycol, propylene glycol, dipropylene glycol, tripropylene glycol, 1,4-butane diol, 1,6-hexane diol, 1,8-octane diol, cyclohexane dimethanol, glycerin, trimethylolpropane, trimethylolethane, pentaerythritol, sorbitol and sucrose, phenol and polyphenolic initiators such as bisphenol A or 1,1,1-tris(hydroxyphenyl)ethane and the like, as well as alkoxylates (especially ethoxylates and/or propoxylates) of any of these that have a hydroxyl equivalent weight less than that of the product of the polymerization, preferably up to 500, more preferably up to 250, even more preferably up to 125, and still more preferably up to 100.

The initiator may be neutralized with or contain a small amount of an acid, particularly if the initiator is prepared in the presence of a base (as is often the case with glycerin). If an acid is present, it may be present in an amount of from about 10 to 100 ppm, based on the weight of the initiator, as described in U.S. Pat. No. 6,077,978. Alternatively, the acid may be used in somewhat larger amounts, such as from 100 to 1000 ppm, again based on the weight of the initiator, as described in US Published Patent Application No. 2005-0209438. The acid may be added to the initiator before or after the initiator is combined with the DMC catalyst and the MG3-15LA compound.

In the present invention, an alkylene oxide is polymerized in the presence of the DMC catalyst complex and the MG3-15LA compound, or a catalyst mixture formed by combining the DMC catalyst complex and the MG3-15LA compound. In some embodiments, enough of the MG3-15LA compound is present to provide at least 0.0005 moles of the magnesium, group 3-group 15 metal or lanthanide series metal per gram of the DMC catalyst complex. A preferred amount is enough to provide at least 0.0025 or at least 0.005 moles of the magnesium, group 3-group 15 metal or lanthanide series metal per gram of the DMC catalyst complex. It is generally not necessary to provide more than 10 moles of magnesium, group 3-group 15 metal or lanthanide series metal compound per gram of the DMC catalyst complex. A preferred upper limit is enough to provide up to 1 mole, up to 0.5 moles or up to 0.25 moles of magnesium, group 3-group 15 metal or lanthanide series metal per gram of DMC catalyst complex. The foregoing amounts do not include any amounts of metals that are included within the DMC catalyst complex.

In some embodiments, the polymerization is performed by forming a catalyst mixture by combining the DMC catalyst complex and the MG3-15LA compound, and polymerizing the alkylene oxide in the presence of this catalyst mixture. The catalyst mixture preferably also contains at least one compound having one or more hydroxyl groups. The compound having one or more hydroxyl groups is preferably (1) an initiator compound as described before, or mixture of initiator compounds, (2) a polyether monol or polyether polyol corresponding to the product of the polymerization, (3) a polyether of intermediate molecular weight between that of the initiator and product, (4) a mixture of two or more thereof. In cases where the catalyst mixture does not contain an initiator, it is necessary to add an initiator compound to the reaction mixture, in addition to the compound having one or more hydroxyl groups. The compound having one or more hydroxyl groups (and any added initiator compound) may be neutralized with or contain a small amount (such as from 10 to 1000 ppm) of an acid, as described in U.S. Pat. No. 6,077,978 and US Published Patent Application No. 2005-0209438.

The catalyst mixture may be heated to a temperature of from 80 to 220° C., preferably from 120 to 180° C. at atmospheric or subatmospheric pressure (the residual being nitrogen or other inert atmosphere) for a period of 10 minutes or more, prior to performing the polymerization. This preliminary heating step is preferably performed in the presence of a compound having one or more hydroxyl groups. This preliminary heating step is preferably performed in the absence of an alkylene oxide. The compound having one or more hydroxyl groups in this preferred process is preferably (1) an initiator compound as described before, or mixture of initiator compounds, (2) a polyether monol or polyether polyol corresponding to the product of the polymerization, (3) a polyether of intermediate molecular weight between that of the initiator and product, or (4) a mixture of two or more of the foregoing. Most preferably, that compound is an initiator compound, and/or a polyether monol or polyether polyol corresponding to the product of the polymerization. This preliminary heating step may cause an alcoholate of the magnesium, group 3-group 15 metal or lanthanide series metal and the initiator compound and/or polyether monol or polyol, as the case may be, to form in situ. This reaction is believed to generate the conjugate acid of some or all of the anion(s) originally present on the starting MG3-15LA compound. Such a conjugate acid preferably is more volatile than the initiator compound or polyether monol or polyether polyol and in such a case is believed to become volatilized under the conditions of the heating step to form a gas which is removed from the mixture during or after the preliminary heating step. The preliminary heating step is particularly preferred when the MG3-15LA compound includes amide anions.

The alkylene oxide polymerization is performed by polymerizing the alkylene oxide in the presence of the catalyst mixture at an elevated temperature. The reaction temperature is typically at least 80° C., preferably at least 120° C., and more preferably at least 140° C. The reaction temperature may be 200° C. or higher, but it is preferred that the temperature does not exceed 190° C., more preferably 180° C., in order to maintain workable reactor pressures, to avoid forming a significant amount of volatile impurities or other by-products, and to maintain adequate catalyst activity without deactivating or decomposing the DMC catalyst. The polymerization reaction usually is performed at superatmospheric pressures, but can be performed at atmospheric pressure or even subatmospheric pressures.

The catalyst mixture can be prepared by combining the double metal cyanide catalyst complex, the MG3-15LA compound and, preferably, a compound containing at least one hydroxyl group in the reaction vessel where the alkylene oxide is to be combined, or in some other vessel.

Enough of the catalyst mixture is used to provide a reasonable polymerization rate, but it is generally desirable to use as little of the double metal cyanide catalyst as possible consistent with reasonable polymerization rates, as this both reduces the cost for the catalyst and, if the catalyst levels are low enough, can eliminate the need to remove catalyst residues from the product. The amount of DMC catalyst complex may be from 1 to 5000 ppm based on the weight of the polyether product. The amount of DMC catalyst complex may be at least 2 ppm, at least 5 ppm, at least 10 ppm, at least 25 ppm, or up to 200 ppm or up to 100 ppm, based on the weight of the polyether product.

The polymerization reaction can be performed batchwise, semi-continuously (including with continuous addition of starter as described in U.S. Pat. No. 5,777,177) or continuously.

In a batch polymerization, the DMC catalyst complex, the MG3-15LA compound, alkylene oxide and initiator are charged to a reaction vessel and heated to the polymerization temperature until the desired molecular weight is obtained. One way of performing a batch polymerization is to combine the DMC catalyst complex, MG3-15LA compound and initiator, optionally in the presence of a polyether having a hydroxyl equivalent weight up to that of the product of the polymerization, and optionally performing a preliminary heating step as described before. The alkylene oxide is then added and the resulting mixture is subjected to polymerization conditions until the alkylene oxide is consumed.

In a semi-batch process, the DMC catalyst complex, MG3-15LA compound and initiator are combined. This mixture preferably undergoes a preliminary heating step as described before. A polyether monol or polyether polyol corresponding to the product of the polymerization, and/or a polyether of intermediate molecular weight between that of the initiator and product, may be present if desired. A portion of the alkylene oxide is introduced into the reaction vessel and the contents of the vessel are heated if necessary to the polymerization temperature. When the DMC catalyst complex has become activated (typically as indicated by a drop of internal reactor pressure), more alkylene oxide is fed to the reactor under polymerization conditions. The alkylene oxide feed is continued until enough has been consumed to reach the target product molecular weight. Additional DMC catalyst and/or MG3-15LA compound may be added during the course of the alkylene oxide addition. In a semi-batch process, the entire amount of initiator is commonly added at the start of the process. After the alkylene oxide feed is completed, the reaction mixture may be cooked down at the polymerization temperature to consume any remaining alkylene oxide.

A batch or semi-batch process is particularly suitable for producing a polyether having a hydroxyl equivalent weight of up to about 400, more preferably up to about 350 or up to about 250, from an initiator compound having a hydroxyl equivalent weight of from 30 to 100, such as diethylene glycol, triethylene glycol, dipropylene glycol, tripropylene glycol, glycerin, trimethylolpropane, pentaerythritol, sucrose or sorbitol, or alkoxylates of any thereof having a hydroxyl equivalent weight of up to 100. However, batch and semi-batch processes also can be used to make polyethers having higher equivalent weights.

A continuous polymerization includes the continuous addition of at least alkylene oxide and starter, and continuous removal of product. A continuous process is generally conducted by establishing steady-state concentrations, within the operational capabilities of the polymerization equipment, of the DMC catalyst, the MG3-15LA compound, initiator, alkylene oxide and polymerizate under polymerization conditions in a continuous reactor such as a loop reactor or a continuous stirred tank reactor. The "polymerizate" is a mixture of polyethers that have molecular weights greater than that of the initiator and up to that of the intended product. Additional DMC catalyst complex, MG3-15LA compound, initiator and alkylene oxide are then continuously added to the reactor. These can be added as a single stream, as separate components, or in various sub-combinations. Additional catalyst mixture can be formed by combining the DMC catalyst complex with the MG3-15LA compound, optionally with the initiator compound, and added during the polymerization. A product stream is continuously withdrawn from the reactor. The rates of the additional stream(s) and product streams are selected to maintain steady-state conditions in the reactor (within the capabilities of the equipment), and to produce a product having a desired molecular weight.

The product stream withdrawn from the continuous reactor may be cooked down for some period of time to allow the unreacted alkylene oxide in that stream to be consumed to low levels.

At the start-up of a continuous process, a mixture formed by combining the DMC catalyst, the MG3-15LA compound and optionally the initiator and/or a polyether may be subjected to a preliminary heating step as described before, before being contacted with the alkylene oxide. DMC catalyst, MG3-15LA compound and initiator that are added during steady-state conditions may also be subjected to such a preliminary heating step prior to introducing them into the reactor.

A continuous process is particularly suitable for producing a polyether product having a hydroxyl equivalent weight from 150 to 5000, especially from 350 to 2500 and still more preferably from 500 to 2000.

In a semi-batch or continuous process as described above, the alkylene oxide may be fed to the reactor on demand by continuously pressurizing the reactor with the alkylene oxide to a predetermined internal reactor pressure. The concentration of unreacted alkylene oxide in a semi-batch or continuous reactor preferably is maintained at a level of from 0.01% to 10%, more preferably from 0.1% to 5% by weight, most preferably from 1 to 3% by weight, during the alkylene oxide feed.

The polymerization reaction can be performed in any type of vessel that is suitable for the pressures and temperatures encountered. In a continuous or semi-continuous process, the vessel should have one or more inlets through which the alkylene oxide and additional initiator compound can be introduced during the reaction. In a continuous process, the reactor vessel should contain at least one outlet through which a portion of the partially polymerized reaction mixture can be withdrawn. A tubular reactor that has multiple points for injecting the starting materials, a loop reactor, and a continuous stirred tank reactor (CTSR) are all suitable types of vessels for continuous or semi-continuous operations. The reactor should be equipped with a means of providing or removing heat, so the temperature of the reaction mixture can be maintained within the required range. Suitable means include various types of jacketing for thermal fluids, various types of internal or external heaters, and the like. A cook-down step performed on continuously withdrawn product is conveniently conducted in a reactor that prevents significant back-mixing from occurring. Plug flow operation in a pipe or tubular reactor is a preferred manner of performing such a cook-down step.

The product obtained in any of the foregoing processes may contain up to 0.5% by weight, based on the total weight, of unreacted alkylene oxide; small quantities of the initiator compound and low molecular weight alkoxylates thereof;

and small quantities of other organic impurities and water. Volatile impurities should be flashed or stripped from the polyether. The product typically contains catalyst residues and residues of the MG-15LA compound. It is typical to leave these residues in the product, but these can be removed if desired. Moisture and volatiles can be removed by stripping the polyol.

The process of the invention is useful for preparing polyether polyol products that can have hydroxyl equivalent weights from as low as about 85 to as high as about 5,000 or more.

When the hydroxyl equivalent weight of the polyether polyol product is somewhat low, such as less than about 400, the concentration of hydroxyl groups during the polymerization reaction tends to be high. For example, the concentration of hydroxyl groups is about 4.25% by weight when the product has an equivalent weight of 400, and this concentration increases to 20% when the product equivalent weight is only 85. Similarly high concentrations of hydroxyl groups are often seen during the early stages of a batch or semi-batch polymerization that produces higher equivalent weight products. An advantage of this invention is that the DMC catalyst is seen to perform well, giving excellent polymerization rates, even when the concentration of hydroxyl groups in the reaction mixture is high, such as in the range of from 4.25 to 20% by weight. As a result, this invention is very amenable to the production of polyether polyol products that have hydroxyl equivalent weights of from 85 to 500, as well as to batch and semi-batch processes in which the concentration of hydroxyl groups is from 4.25 to 20% by weight in the early stages of reaction.

The polymerization reaction can be characterized by the "build ratio", which is defined as the ratio of the number average molecular weight of the polyether product to that of the initiator compound. This build ratio may be as high as 160, but is more commonly in the range of from 2.5 to about 65 and still more commonly in the range of from 2.5 to about 50. The build ratio is typically in the range of from about 2.5 to about 15, or from about 7 to about 11 when the polyether product has a hydroxyl equivalent weight of from 85 to 400. When glycerin is the initiator, a preferred build ratio is from 2.5 to 11.5, especially from 4 to 11.5.

Certain initiators may provide specific advantages. Triethylene glycol, for example, has been found to be an especially good initiator for use in batch and semi-batch processes for producing polyether diols. Tripropylene glycol has been found to be an especially good initiator for use in making a catalyst mixture by combining initiator, DMC catalyst and the MG3-15LA compound.

Polyether polyols produced in accordance with the invention are useful for making polyurethanes, among other things. Higher equivalent weight (500-3000 g/equivalent) polyether polyol products are useful in making elastomeric or semi-elastomeric polyurethane, including noncellular or microcellular elastomers, and flexible polyurethane foams. The flexible polyurethane foams may be made in a slabstock or molding process. Polyether polyol products having equivalent weights of about 225 to 400 are useful in making semi-flexible foams as well as the so-called viscoelastic or "memory" foams. Polyether polyols having equivalent weights of from 85 to 400 are useful in making rigid polyurethane foams, such as thermal insulating foams for appliances, buildings, ship hulls and the like, as well as in various coating, adhesive, sealant and elastomer products. The polyether polyols tend to have properties quite similar to those made in conventional DMC-catalyzed polymerization process and in alkali metal hydroxide-catalyzed polymerization processes.

Polyether monols produced in accordance with the invention are useful as surfactants or as industrial solvents, among other uses.

The following examples are provided to illustrate the invention but are not intended to limit the scope thereof. All parts and percentages are by weight unless otherwise indicated.

EXAMPLE 1 AND COMPARATIVE RUN A

Comparative Run A: Into the shell of a 500 ml Autoclave Engineers reactor are placed 90 g of a 255 molecular weight polypropylene oxide) triol (Voranol® CP260, The Dow Chemical Company), 3.5 microliters of a 0.15 M phosphoric acid solution in water, and 0.0249 g of a zinc hexacyanocobaltate catalyst complex marketed by Bayer Material Science, Inc. as Arcol 3 catalyst. The shell of the reactor is then placed on the reactor frame, and the reaction mixture is stirred and heated at a temperature of 145° C. for 90 minutes with a slow purge of nitrogen (0.5 standard cubic feet per hour) passing through the reactor contents. The reactor contents are heated to 149° C.±1.5° C., and, while maintaining that temperature, enough propylene oxide (PO) is introduced into the reactor to produce an internal reactor pressure of 20.5±0.5 psig (141±3.49 kPa), at which time the reactor is sealed. The pressure inside the reactor is monitored. The amount of time required for the internal reaction pressure to decline to about 10.25 psig (70.5 kPa) (1 hour and 4 minutes) is recorded as the time to catalyst activation. Still maintaining a temperature of 149° C.+/−1.5° C., a PO feed is introduced into the reactor, at a rate sufficient to maintain an internal reactor pressure of 27+/−3 psig (186±20.7 kPa). This feed is continued until a total of 76.6 mL (65.8) g of PO (including the initial PO charge) has been fed into the reactor. The time required to complete the PO feed (12 hours, 20 minutes) is measured as an indication of polymerization rate. After all the PO has been fed into the reactor, the reaction mixture is cooked down at 149° C.±1.5° C. in an attempt to complete the polymerization; however, a steady internal reactor pressure (indicative of complete polymerization of the charged PO) is not achieved after 4½ hours. The failure to reach a steady internal reactor pressure indicates that the catalyst has become substantially deactivated.

Example 1 is performed in the same manner, except this time 0.189 g of aluminum isopropoxide (0.037 moles/g of DMC catalyst complex) is added to the reactor after the DMC catalyst is added and thoroughly mixed into the reaction mixture before it is heated. In this case, the activation time is 89 minutes, but the PO feed requires only 2½ hours and a steady internal reaction pressure is achieved after cooking the reaction mixture down for only 28 minutes. The product has a number average molecular weight of about 450.

The addition of the aluminum isopropoxide is seen to very substantially increase the rate of PO polymerization.

EXAMPLES 2 AND 3

Example 2: Into the shell of a 500 ml Autoclave Engineers reactor are placed 90 g of a propoxylate of glycerin that has an average molecular weight of 260 (Voranol® CP230-660, The Dow Chemical Company). This polyol is a mixture of propoxylates having molecular weights from 150 to 614, and contains 2% by weight glycerin. 3.6 microliters of a 0.15 M phosphoric acid solution in water and 100 parts per million, based on the expected mass of the product, of the Arcol 3 catalyst are added. 0.0075 mole of aluminum isopropoxide/gram of DMC catalyst complex (enough to provide 20 parts per million aluminum based on the expected mass of the product) is added and stirred in. The shell of the reactor is then placed on the reactor frame, and the reaction mixture is stirred and heated at a temperature of 145° C. for 90 minutes with a slow purge of nitrogen (0.5 standard cubic feet per hour) passing through the reactor contents. The reactor contents are heated to 140° C., and, while maintaining that temperature, enough PO is introduced into the reactor to produce an internal reactor pressure of 20.5+/−0.5 psig (141±3.49 kPa), at which time the reactor is sealed. The pressure inside the reactor is monitored. The amount of time (153 minutes) required for internal reaction pressure to decline to about 10.25 psig (70.5 kPa) is recorded as the time to catalyst activation. Still maintaining a temperature of 140° C., a PO feed is introduced into the reactor, at a rate sufficient to maintain an internal reactor pressure of 27±3 psig (186±20.7 kPa). This feed is continued until a total of 76.6 mL (65.8) g of PO (including the initial PO charge) has been fed into the reactor. The time required to complete the PO feed after the catalyst has become activated is 5 hrs and 17 minutes. After all the PO has been fed into the reactor, the reaction mixture is cooked down at 140° C. for 88 minutes, until a steady internal reactor pressure (indicative of complete polymerization of the charged PO) is achieved. A 450 number average molecular weight product is obtained having a polydispersity of 1.1.

Example 3 is performed in the same manner, except that the amount of the aluminum isopropoxide is increased to 0.1875 moles per gram of DMC catalyst complex (500 ppm of aluminum based on the expected mass of the product). A 450 number average molecular weight product having a polydispersity of 1.08 is obtained. The activation time in this case is 61 minutes; the time to feed the PO after the catalyst complex has become activated is 3 hours and 16 minutes, and the cook down time is 29 minutes. The higher amount of aluminum isopropoxide in Example 3 is seen to provide for both a faster activation of the catalyst as well as a faster polymerization rate after the catalyst has become activated.

EXAMPLES 4 AND 5

Example 4 is performed in the same manner as Example 2, except the polymerization temperature is 160° C. The activation time is 68 minutes, the additional time to feed PO is 3 hours and 24 minutes, and the cook down time at the end of the batch is 20 minutes.

Example 5 is performed in the same manner as Example 3, except the polymerization temperature is 160° C. The activation time is 22 minutes, the additional time to feed PO is less than 4 hours, and the cook down time at the end of the batch is 21 minutes.

EXAMPLES 6 AND 7

Example 6 is performed in the same manner as Example 2, except the polymerization temperature is 160° C., the amount of DMC catalyst complex is 220 parts per million, based on the expected mass of the product, and the amount of aluminum isopropoxide is enough to provide 44 parts per million aluminum based on the expected mass of the product (0.0165 mole of aluminum isopropoxide/gram of DMC catalyst complex). The activation time is 21 minutes, the time needed to feed the PO after the catalyst has become activated is 2 hours and 30 minutes, and the cook down time at the end of the batch is 21 minutes.

Example 7 is performed in the same manner as Example 6, except the amount of aluminum isopropoxide is enough to provide 1100 parts per million aluminum based on the expected mass of the product (0.4125 mole of aluminum isopropoxide/gram of DMC catalyst complex). The activation time is 28 minutes, the time needed to feed the PO after the catalyst has become activated is 2 hours and 5 minutes, and the cook down time at the end of the batch is 30 minutes.

EXAMPLE 8 AND COMPARATIVE RUN B

Into the shell of a 500 mL Autoclave Engineers reactor are placed 5 g of sorbitol and 95 g of a propoxylated sorbitol that has an average equivalent weight of 117 (Voranol® RN 482, The Dow Chemical Company). 5.3 microliters of a 0.15 M phosphoric acid solution in water. The shell of the reactor is then placed on the reactor frame, and the reactor contents are heated to 60° C. for one hour with stirring and with a slow purge of nitrogen (0.5 standard cubic feet per hour). The reactor contents are cooled to 40° C. and 0.0286 g of the Arcol 3 catalyst are added, followed by 0.108 g of aluminum isopropoxide (0.0185 moles per g of DMC catalyst complex). The reaction mixture is heated to 60° C. with stirring and a nitrogen purge and then allowed to cool to 20° C., at which temperature stirring under nitrogen is continued overnight. The reaction mixture is then stirred and heated at a temperature of 145° C. for 90 minutes with a slow purge of nitrogen (0.5 standard cubic feet per hour) passing through the reactor contents. The nitrogen purge is discontinued, the reactor contents are heated to 150° C., and, while maintaining that temperature, 11.1 mL of PO is introduced at the rate of 1 mL/minute to produce an internal reactor pressure of 29.5 psig (203 kPa), at which time the reactor is sealed. The mixture is stirred for 90 seconds and then the PO addition is resumed at the rate of 0.05 mL/minute. Five minutes after the PO addition is resumed, the pressure inside the reactor drops to 28.7 psig (198 kPa) (indicating that the catalyst has become activated) and at that time the PO addition rate is increased again to 0.10 mL/minute. The pressure inside the reactor is monitored. Once the pressure reaches 34 psig (234 kPa), the PO addition rate is again decreased to 0.07 mL/minute, until a total of 16.7 mL of PO has been added. The PO feed is then stopped, and the reactor contents stirred at 150° C. until the reactor declines to 1.95 psig (13.4 kPa) (4 hours and 20 minutes). A 450 number average molecular weight product is obtained.

Comparative Run B is performed in the same general manner, except that no aluminum isopropoxide is added and the PO is fed slightly differently. In Comparative Run B, 12 mL of PO is added at the rate of 1.0 mL/minute to charge the reactor to 29 psig (203 kPa). 2.5 hours at 150° C. are needed to activate the catalyst (as indicated by a drop in internal reactor pressure to 28.7 psig (198 kPa)), and then 2.2 mL PO is fed at 0.1 mL/minute. After all the PO is added, the reactor is cooked down for 6½ hours, at which time the reactor pressure has only declined to 24.2 psig (167 kPa), indicating a very slow polymerization, compared with Example 8.

EXAMPLE 9 AND COMPARATIVE RUN C

Example 9: Into the shell of a 10-liter stainless steel alkoxylation reactor are placed 3143 g of the Voranol® CP-260 polyol described before and 0.36 grams of an 85% by weight phosphoric acid solution in water. The shell of the reactor is then placed on the reactor frame and the reactor contents are heated to 150° C. for thirty minutes under vacuum. 1.099 g of the Arcol 3 catalyst is separately mixed into 390 g of the same Voranol CP-260 polyol and added to the reactor, which is then kept under vacuum at 150° C. for one hour. 8.4 g of aluminum isopropoxide (0.037 moles/g DMC catalyst complex) are mixed into another 523 g of the polyol and added to the reactor. The reactor contents are then heated at 150° C. under vacuum for about 45 minutes. 452 g of PO are fed to the reactor at the rate of 60 g/minute while maintaining the temperature at 150° C. When the reactor pressure declines to 0.3 bar (30 kPa), 2550 g of PO are fed in over 59 minutes. The reactor contents are then digested at 150° C. for 2 hours, and the product is then cooled down and digested. The hydroxyl number of the resulting product is 372 mg KOH/g (452 molecular weight); its viscosity is 368 cSt at 25° C.

Comparative Run C is performed in the same general manner. The initial charge to the reactor consists of 3066 g of the Voranol® CP-260 polyol described before and 0.31 grams of an 85% by weight phosphoric acid solution in water. The shell of the reactor is then placed on the reactor frame, and the reactor contents are heated to 130° C. for three hours under vacuum. 0.966 g of the Arcol 3 catalyst is separately mixed into 476 g of the same Voranol CP-260 polyol and added to the reactor, which is then kept under vacuum at 150° C. for thirty minutes. 394 g of PO are fed to the reactor at the rate of 60 g/minute while maintaining the temperature at 150° C. When the reactor pressure declines to 0.3 bar 30 kPa), 2220 g of PO are fed in over 139 minutes. The lower PO addition rate reflects the much slower polymerization rate in this run, compared to Example 9. The reactor contents are then digested at 150° C. for 2 hours, and the product is then cooled down and collected.

The hydroxyl number of the resulting product is 380 mg KOH/g (443 molecular weight); its viscosity is 360 cSt at 25° C. The products of Example 9 and Comparative Run C therefore are essentially identical.

EXAMPLE 10 AND COMPARATIVE RUN D

Example 10: 60 grams of a 450 molecular weight poly (propylene oxide) triol acidified with 300 ppm of an 85% phosphoric acid solution in water, 0.030 g of the Arcol 3 catalyst and 37.5 microliters of a 1 M solution of diethyl zinc in hexane are mixed with stirring for 10 minutes at 130° C. Fifty grams of this mixture are transferred to a 300 mL pressure reactor, where it is heated to 160° C. with stirring and sparged with nitrogen for two hours. PO is then pumped into the reactor at the rate of 0.25 mL/minute. After about 2 mL have been added, glycerin that has been acidified with 70 ppm phosphoric acid is fed into the reactor at the rate of 0.44 mL/minute. The pressure in the reactor is monitored during the PO and glycerin feeds. The pressure remains below 20 psig (138 kPa) for well over 150 minutes, is still below 40 psig (276 kPa) after 200 minutes, and reaches 53 psig (365 kPa) after 245 minutes of the feeds. At this time the feeds are discontinued and the reactor contents are digested at 160° C. for one hour. 110 g of polyol are obtained. The DMC catalyst loading in the product is 227 ppm.

Comparative Run D is performed in the same manner, except the diethyl zinc solution is omitted. In this case, the pressure in the reactor increases much more rapidly than is seen in Example 10, reaching 44 psig (303 kPa) after only 109 minutes. The faster increase in reactor pressure indicates a significantly slower polymerization rate than is seen in Example 10. The feeds are discontinued at this point, and 73 g of a polyol that contains 342 ppm of the DMC catalyst are obtained. Comparative Run D polymerizes more slowly, produces less product per unit time, and requires a higher catalyst level than Example 10.

EXAMPLE 11 AND COMPARATIVE RUN E

Example 11: 60 grams of a 700 molecular weight poly (propylene oxide) triol (Voranol® 270, The Dow Chemical Company) and 0.015 g of the Arcol 3 catalyst are stirred together. 4.3 mg of an 85% phosphoric acid solution in water are added and the mixture is stirred again. Then, 0.61 mL of a 1.6 M solution of diethylaluminum ethoxide in toluene is added, followed by stirring for 10 minutes at 130° C. Fifty grams of this mixture are transferred to a 300 mL pressure reactor, where it is heated to 150° C. with stirring and sparged with nitrogen for two hours. PO is then pumped into the reactor at the rate of 1.0 mL/minute. After about 28 mL of PO have been added, glycerin that has been acidified with 70 ppm phosphoric acid is fed into the reactor at the rate of 0.061 mL/minute while continuing the PO feed. Propylene oxide pressures in the reactor remain well below 20 psig (138 kPa) during this addition. After about 100 minutes of the PO and glycerin feeds, the feeds are discontinued for about 5 minutes, and then resumed at the same feed rates for approximately 10 more minutes. The reactor contents are then allowed to digest at 150° C. Internal reactor pressure rapidly decreases to about zero, indicating that the catalyst remains active and the remaining PO polymerizes quickly. After digesting for about 60 minutes, the PO and glycerin feeds are again resumed at half their previous rates, for about one hour. Again propylene oxide pressures remain below 20 psig (138 kPa) as the PO and glycerin are fed to the reactor. The product has a molecular weight of about 1100.

When Example 11 is repeated without the diethylaluminum ethoxide (Comparative Run E), propylene oxide pressure inside the reactor builds to 30 psig (207 kPa) after about 55 minutes of the PO and glycerin feeds. This pressure build-up indicates that the catalyst is performing sluggishly and cannot polymerize the PO at the rate at which it is being fed in. After digesting the reactor contents for about 40 minutes, the PO and glycerin feeds are resumed at one-half the initial rates, and the internal reactor pressure is again seen to rise as the reactants are fed.

EXAMPLES 12 AND 13 AND COMPARATIVE RUN F

Example 12: 50 grams of a 700 molecular weight poly (propylene oxide) triol (Voranol® 270, The Dow Chemical Company) that is acidified with 100 ppm phosphoric acid and 0.0125 g of the Arcol 3 catalyst are stirred together in a 300 mL pressure reactor. Then, 37.5 mg of aluminum isopropoxide (about 0.147 moles/gram DMC catalyst complex) are added, and the resulting mixture is heated to 150° C. with stirred and sparged with nitrogen for two hours. PO is then pumped into the reactor at the rate of 0.5 mL/minute. After about 28 mL of PO have been added, glycerin that has been acidified with 70 ppm phosphoric acid is fed into the reactor at the rate of 0.03 mL/minute. These feeds are continued for about 200 minutes, until a total of 130 mL of PO has been fed into the reactor. Pressures in the reactor remain well below 10 psig (69 kPa) during this entire addition. After a short digestion at 150° C., an 1100 molecular weight polyol is obtained.

Example 13 is performed in the same manner, except that the amount of aluminum isopropoxide is increased to 111 mg (about 0.44 moles aluminum/g DMC catalyst complex), and after digesting at 150° C., additional PO is fed at the rate of 0.5 mL/minute for about 60 minutes. Internal reactor pressures remain under 20 psig (138 kPa) during the entire polymerization, once the catalyst has become activated. An 1100 molecular weight polyol is obtained.

Comparative Run F is run in the same manner, except no aluminum isopropoxide is provided, the propylene oxide feed rate is only 0.35 mL/minutes and the glycerin feed rate is only 0.02 mL/minute. Catalyst activation is slower than in Examples 12 and 13, and reactor pressure increases to 30 psig (207 kPa) after about 70 minutes of the PO/glycerin feeds. The feeds are discontinued when the pressure reaches 30 psig (207 kPa), and the reactor contents are digested until the reactor pressure falls to approximately zero. The PO and glycerin feeds are then re-started, and again the internal reactor pressure increases rapidly to 30 psig (207 kPa).

EXAMPLE 14

Into the shell of a 500 mL Autoclave Engineers reactor are placed 74.3 g of a 450 molecular weight polypropylene oxide triol) (Voranol® CP-450, The Dow Chemical Company). 2.85 microliters of a 0.15% by weight phosphoric acid solution in water and 0.035 of the Arcol 3 catalyst. After stirring, 0.265 g (about 0.37 moles/gram of DMC catalyst complex) aluminum isopropoxide are added, and the mixture is stirred again. The shell of the reactor is then placed on the reactor frame, and the reactor contents are heated to 140° C. for 90 minutes with stirring and with a slow purge of nitrogen (0.5 standard cubic feet per hour). The reaction mixture is heated to 159° C. with stirring and, while maintaining that temperature, 50.8 mL of PO is introduced at the rate of 1 mL/minute. The catalyst activates before the internal reactor pressure reaches 10 psig (69 kPa). Once the catalyst has become activated (as evidenced by a drop in the internal reactor pressure), the PO feed rate is decreased to 0.5 mL/minute and a glycerin feed (0.063 g/minute) is begun. The PO and glycerin feeds are continued for 2.5 hours, during which time the internal reactor pressure increases only to 9 psig (62 kPa). The PO feed rate is increased to 1.03 mL/minute and the glycerin feed rate is increased to 0.127 g/minute for 90 minutes, during which time the internal reactor pressure increases to only 15 psig (103 kPa). At this point the PO and glycerin feed rates are again increased, to 1.29 mL/minute and 0.158 g/minute, respectively, resulting in a slow increase in internal reactor pressure to 23.5 psig (162 kPa). The reaction contents are digested at 159° C. for 30 minutes. The total PO feed is 252.7 mL and the total amount of glycerin fed is 31.3 g. Total co-feed time is 5 hours. 340 g of polyol are obtained (97% yield). The polyol molecular weight is 700, with a polydispersity of 1.13.

EXAMPLE 15

Into the shell of a 500 ml Autoclave Engineers reactor are placed 66.7 g of a 255 molecular weight polypropylene oxide triol) (Voranol® CP-260, The Dow Chemical Company), 3.0 microliters of a 0.15% by weight phosphoric acid solution in water and 0.035 of a zinc hexacyanocobaltate catalyst complex. After stirring, 0.265 g (about 0.37 moles/gram of DMC catalyst complex) aluminum isopropoxide are added, and the mixture is stirred again. The shell of the reactor is then placed on the reactor frame, and the reactor contents are heated to 145° C. for 90 minutes with stirring and with a slow purge of nitrogen (0.5 standard cubic feet per hour). The reaction mixture is heated to 164° C. with stirring and, while maintaining that temperature, PO is introduced at the rate of 1 mL/minute until the internal reactor pressure reaches 20.3 psig (140 kPa), at which time the PO feed rate is decreased to 0.5 mL/minute. When the internal reactor pressure declines to 18 psig (124 kPa), the PO feed rate is increased to 0.75 mL/minute, and the reactor pressure continues to decline. After a total of 60.1 mL of PO has been added, the PO feed rate is decreased to 0.25 mL/minute and a glycerin feed (0.05 g/minute) is begun. The internal reactor pressure at the point the glycerin feed is begun is only 2.8 psig (19 kPa). The PO and glycerin feeds are continued until the internal reactor pressure increases to 44.5 psig (307 kPa), at which point the reactor contents are digested at 164° C. for 55 minutes. The total feed time is 7 hours and 10 minutes. The product polyol has a molecular weight of 449, a polydispersity of 1.09, and contains 152 ppm of the DMC catalyst complex.

EXAMPLE 16 AND COMPARATIVE RUN G

Example 16: Into the shell of a 500 ml Autoclave Engineers reactor are placed 90 g of a 255 molecular weight polypropylene oxide triol) (Voranol® CP-260, The Dow Chemical Company), 3.5 microliters of a 0.15% by weight phosphoric acid solution in water and 0.0249 of the Arcol 3 catalyst. After stirring, 0.085 g (about 0.011 moles/gram of DMC catalyst complex) of stannous ethyl hexanoate are added, and the mixture is stirred again. The shell of the reactor is then placed on the reactor frame, and the reactor contents are heated to 145° C. for 90 minutes with stirring and with a slow purge of nitrogen (0.5 standard cubic feet (14 liters) per hour). The reaction mixture is heated to 149° C. with stirring and, while maintaining that temperature, PO is introduced until the internal reactor pressure reaches 20.5 psig (141 kPa), at which time the PO feed rate is stopped and the reactor contents digested at 149° C. The reactor pressure decreases to about 10 psig (69 kPa) after 3 hours and 53 minutes. PO is then fed into the reactor for 3 hours and 19 minutes, at a rate which maintains a reactor pressure of 27±3 psig (186±20.7 kPa). The reactor contents are then digested for 40 minutes until a constant PO pressure of near zero is obtained. The total amount of PO charged to the reactor is 79.7 mL.

Comparative Run G is performed in the same manner, except the stannous ethyl hexanoate is omitted. The catalyst activates in 50 minutes, but the PO feed requires 11 hours and 40 minutes. After a total of 79.7 mL of PO is introduced to the reactor, the reactor contents are digested for 4.5 hours to achieve a constant internal reactor pressure. The slow feed rates and long digestion time indicate that the catalyst is much more sluggish that in Example 16.

EXAMPLE 17

Into the shell of a 500 ml Autoclave Engineers reactor are placed 90 g of a 255 molecular weight polypropylene oxide triol) (Voranol® CP-260, The Dow Chemical Company), 3.5 microliters of a 0.15% by weight phosphoric acid solution in water and 0.0249 of the Arcol 3 catalyst. After stirring, 0.038 g (about 0.008 moles/gram of DMC catalyst complex) of stannous methoxide is added, and the mixture is stirred again. The shell of the reactor is then placed on the reactor frame, and the reactor contents are heated to 145° C. for 90 minutes with stirring and with a slow purge of nitrogen (0.5 standard cubic feet (14 liters) per hour). The reaction mixture is heated to 149° C. with stirring and, while maintaining that temperature, PO is introduced until the internal reactor pressure reaches 20.5 psig (141 kPa), at which time the PO feed rate is stopped and the reactor contents digested at 149° C. The reactor pressure decreases to about 10 psig (69 kPa) after 1 hour and 39 minutes. PO is then fed into the reactor for 3 hours, at a rate which maintains a reactor pressure of 27±3 psig (186±20.7 kPa). The reactor contents are then digested for 20 minutes until a constant PO pressure of near zero is obtained. The total amount of PO charged to the reactor is 79.7 mL. The resulting polyol has a molecular weight of 436 and a polydispersity of 1.1.

EXAMPLE 18

150 grams of a 260 molecular weight poly(propylene oxide) triol (Voranol® CP-260) is acidified with 300 ppm of an 85% phosphoric acid solution in water, and mixed with 0.052 g of the Arcol 3 catalyst. 306 microliters of a 1 M solution of diethyl zinc in hexane (about 0.006 moles Zn/g DMC catalyst complex) are then mixed in, and the resulting mixture is heated under nitrogen at 130° C. for 15 minutes. 57.8 grams of this mixture are transferred to the shell of a 500 mL pressure reactor, where it is heated to 145° C. with stirring and sparged with nitrogen for 90 minutes. The reaction mixture is heated to 164° C. with stirring and, while maintaining that temperature, PO is fed into the reactor at the rate of 1.0 mL/minute. The catalyst activates immediately, and the reactor pressure remains at or below 7.2 psig (50 kPa). The PO feed rate is decreased to 0.27 mL/minute and a glycerin co-feed is introduced at the rate of 0.056 g/minute. The PO and glycerin feeds are continued for 3 hours and 33 minutes, until the internal reactor pressure reaches 50 psig (345 kPa), at which time the PO feed rate is stopped and the reactor contents digested at 164° C. The total amount of PO charged to the reactor is 51.1 mL. The resulting polyol has a molecular weight of about 450 and contains about 132 ppm of the DMC catalyst complex.

EXAMPLE 19

Into the shell of a 500 ml Autoclave Engineers reactor are placed 50 g of a 400 molecular weight poly(propylene oxide) diol (Voranol® P-400, The Dow Chemical Company), 5.0 grams of propylene glycol, 0.23 microliters of a 0.15% by weight phosphoric acid solution in water, 0.02 g of the Arcol 3 catalyst and 0.151 g (about 0.037 moles/gram of DMC catalyst complex) of aluminum isopropoxide. The shell of the reactor is then placed on the reactor frame, and the reactor contents are heated to 145° C. for 90 minutes with stirring and with a slow purge of nitrogen (0.5 standard cubic feet (14 liters) per hour). The reaction mixture is heated to 150° C. with stirring and, while maintaining that temperature, 32.4 mL of PO is introduced at the rate of 1 mL/minute. The PO begins to react immediately, and the internal reactor pressure reaches only 15 psig (103 kPa) during the initial PO feed. The reactor temperature is then increased to 160° C., and PO and propylene glycol are co-fed to the reactor at a weight ratio of 4.26 g PO per gram of propylene glycol, until a total of 118.4 mL PO and 22.6 g of propylene glycol have been added. The addition rates are varied to maintain a reactor pressure of 25±4 psig (172±27.6 kPa) in the reactor during the co-feed. It takes 10 hours to complete the co-feed, and an additional hour of digestion at 160° C. to obtain a constant internal reaction pressure. The product has a molecular weight of about 400 and contains about 100 ppm of the DMC catalyst complex.

EXAMPLES 20-21 AND COMPARATIVE RUN H

Example 20: Into the shell of a 500 ml Autoclave Engineers reactor are placed 90 g of a propoxylate of glycerin that has an average molecular weight of 260 (Voranol® CP230-660, The Dow Chemical Company). 3.5 microliters of a 0.15 M phosphoric acid solution in water and 0.0249 g of the Arcol 3 catalyst are added. 0.041 mole of aluminum sec-butoxide/gram of DMC catalyst complex (enough to provide 160 parts per million aluminum based on the expected mass of the product) is added and stirred in. The shell of the reactor is then placed on the reactor frame, and the reaction mixture is stirred and heated at a temperature of 145° C. for 90 minutes with a slow purge of nitrogen (0.5 standard cubic feet per hour) passing through the reactor contents. The reactor contents are heated to 150° C., and, while maintaining that temperature, enough propylene oxide (PO) is introduced into the reactor to produce an internal reactor pressure of 20.5±0.5 psig (141±3.49 kPa), at which time the reactor is sealed. The pressure inside the reactor is monitored. The time to catalyst activation is 40 minutes. Still maintaining a temperature of 150° C., a PO feed is introduced into the reactor, at a rate sufficient to maintain an internal reactor pressure of 25±3 psig (172±20.7 kPa). This feed is continued until a total of 79.7 ml (65.8) g of PO (including the initial PO charge) has been fed into the reactor. The time required to complete the PO feed after catalyst activation is 3 hrs and 15 minutes. After all the PO has been fed into the reactor, the reaction mixture is cooked down at 150° C. until a steady internal reactor pressure (indicative of complete polymerization of the charged PO) is achieved. The PO digest time for this reaction is 30 minutes. A 450 number average molecular weight product having a polydispersity of 1.1 is obtained.

EXAMPLE 21

Into the shell of a 500 ml Autoclave Engineers reactor are placed 90 g of a propoxylate of glycerin that has an average molecular weight of 260 (Voranol® CP230-660, The Dow Chemical Company). 3.5 microliters of a 0.15 M phosphoric acid solution in water, and 0.0249 g of the Arcol 3 catalyst are added. 0.0042 mole of stannous pyrophosphate/gram of DMC catalyst complex (0.0021 moles of tin/gram of DMC catalyst complex; enough to provide 160 parts per million of tin (II) based on the expected mass of the product) is added and stirred in. The shell of the reactor is then placed on the reactor frame, and the reaction mixture is stirred and heated at a temperature of 145° C. for 90 minutes with a slow purge of nitrogen (0.5 standard cubic feet (14 liters) per hour) passing through the reactor contents. The reactor contents are heated to 150° C., and, while maintaining that temperature, enough propylene oxide (PO) is introduced into the reactor to produce an internal reactor pressure of 20.5±0.5 psig (141±3.49 kPa), at which time the reactor is sealed. The pressure inside the reactor is monitored. The time to catalyst activation is 27 minutes. Still maintaining a temperature of 150° C., a PO feed is introduced into the reactor, at a rate sufficient to maintain an internal reactor pressure of 25±3 psig (172±20.7 kPa). This feed is continued until a total of 79.7 mL (65.8) g of PO (including the initial PO charge) has been fed into the reactor. The time required to complete the PO feed after catalyst activation is 6 hrs and 50 minutes. After all the PO has been fed into the reactor, the reaction mixture is cooked down at 150° C. until a steady internal reactor pressure (indicative of complete polymerization of the charged PO) is achieved. The PO digest time for this reaction is 77 minutes. A 403 number average molecular weight product is obtained having a polydispersity of 1.07.

Comparative run H is performed in the same manner as Example 20, except this time no aluminum sec-butoxide is added to the reactor. In this case, the activation time is 40 minutes, but the PO feed requires 9 hrs and 17 minutes and a steady internal reaction pressure is not achieved after cooking the reaction mixture down for more than 35 minutes. The product has a number average molecular weight of about 450.

The addition of the aluminum sec-butoxide or stannous pyrophosphate is seen to very substantially increase the rate of PO polymerization.

EXAMPLES 22-29 AND COMPARATIVE RUNS I-O

Additive screening tests (Examples 22-26 and 29) are performed in a 48-well Symyx Technologies Parallel Pressure Reactor equipped with a syringe pump connected to a robotically controlled needle with compressed microvalve for injection of propylene oxide. Additives are screened at a loading of 25.4 micromoles in each well. In each case, 36 mg of the Arcol 3 catalyst, 74.16 g of a 700 molecular weight polypropylene oxide) triol (Voranol® 270), and 10 microliters of phosphoric acid are mixed and heated at 130° C. for 30 minutes with stirring. 2 mL of the resulting suspension is added to a reactor tube containing the additive, followed by 20 microliters of glycerol. The tubes are then loaded into the reactor and heated to 150° C. 0.66 mL of propylene oxide is added to each well all at once. The reaction mixture is heated for 4 hours at 150° C., cooled to room temperature, and vented. The pressure inside each well is monitored during the heating. The time at which a large pressure drop is seen is taken as the time of catalyst activation.

Example 27 is performed in the same general manner, except aluminum isopropoxide (4.9 mmol), zinc methoxide (7.8 mmol) and DMC (250 ppm) in a mixture of Voranol 270 acidified 100 ppm $H_3PO_4$ (2 mL), 20 mL glycerol and PO (0.5 mL) at 150° C. are used.

Example 28 is performed in the same general manner, except diantimony tris(ethylene glycolate) (7.75 mmol) and DMC (250 ppm) in a mixture of Voranol 270 acidified 100 ppm $H_3PO_4$ (2 mL), 20 mL glycerol and PO (0.5 mL) at 150° C. are used.

The Comparative Runs are performed in the same manner, either without the DMC catalyst (Comparative Runs I-N) or without any additive (Comparative Run O).

The additives screened in each case, and the results obtained, are as indicated in Table 1 below.

TABLE 1

| Example or Comparative Run | Additive Type | DMC catalyst | Time to activation |
|---|---|---|---|
| 22 | Diethylaluminum ethoxide | Present | Less than 40 minutes |
| 23 | Aluminum isopropoxide | Present | Approximately 30 minutes |
| 24 | Hafnium tetra t-butoxide | Present | Approximately 30 minutes |
| 25 | Zirconium tetra t-butoxide | Present | Less than 40 minutes |
| 26 | Titanium tetra t-butoxide | Present | Approximately 50 minutes |

TABLE 1-continued

| Example or Comparative Run | Additive Type | DMC catalyst | Time to activation |
|---|---|---|---|
| 27 | Aluminum isopropoxide and zinc methoxide | Present | Approximately 15 minutes |
| 28 | Antimony (III) glycolate | Present | Approximately 2 hours |
| 29 | Diethyl zinc | Present | Approximately 10 minutes |
| I | Diethylaluminum ethoxide | None | Minimal polymerization within 4 hours |
| J | Aluminum isopropoxide | None | Minimal polymerization within 4 hours |
| K | Hafnium tetra t-butoxide | None | Minimal polymerization within 4 hours |
| L | Zirconium tetra t-butoxide | None | Minimal polymerization within 4 hours |
| M | Titanium tetra t-butoxide | None | Minimal polymerization within 4 hours |
| N | Diethyl zinc | None | Minimal polymerization within 4 hours |
| O | None | Present | No activation within 4 hours |

As can be seen from the data in Table 1, the DMC catalyst by itself fails to activate within four hours (Comparative Run O), but activates rapidly when any of the additives are present. Comparative Runs I-N demonstrate that the additives by themselves are ineffective PO polymerization catalysts.

EXAMPLE 30 AND COMPARATIVE RUN P

Comparative Run P: Into a jar containing 30 g of a 700 molecular weight poly(propylene oxide) triol (Voranol 270, from The Dow Chemical Company) acidified with 100 ppm $H_3PO_4$ is added 24.8 mg of zinc chloride (0.0243 moles zinc/gram of DMC catalyst complex). 7.5 mg of the Arcol 3 catalyst is then added and the mixture is heated at 150° C. for 1.25 hours under a nitrogen flow. 2 mL of the resulting suspension is added to a reactor tube containing 20 microliters of glycerol. The tubes are then heated to 150° C. 0.50 mL of propylene oxide is added to all at once. The reaction mixture is heated for 3.5 hours at 150° C., cooled to room temperature, and vented. The pressure inside the tube is monitored during the heating. Even after 200 minutes, there is barely any pressure drop within the tube, which indicates that the DMC catalyst has failed to activate.

Example 30 is performed in the same manner, substituting 12.1 micromoles of diethyl zinc for the zinc chloride. In this case a large pressure drop, indicating that the catalyst has become activated, is seen within 20 to 30 minutes after the alkylene oxide is added.

EXAMPLES 31-32 AND COMPARATIVE RUN R

Example 31: 120 grams of a 700 molecular weight polypropylene oxide) triol are mixed with 30 mg of phosphoric acid, 20 mg of the Arcol 3 catalyst and 0.35 g of hafnium tetra(tert-butoxide). 100 grams of the mixture are placed into the shell of a 600 mL pressure reactor and heated under a nitrogen sparge for 140° C. for 90 minutes. Nitrogen pressure is relieved to zero gauge pressure. Propylene oxide is fed into the reactor at a rate of 0.7 mL/minute of propylene oxide for 10 minutes, while keeping the reactor temperature at 140° C. The reactor is then maintained at the same temperature until a sharp drop in internal reactor pressure is seen, indicating that the catalyst has become activated. More propylene oxide is then added, at the same temperature and at a flow rate of 1.5 mL/minutes until approximately 380 mL has been added. The reactor contents are then digested at 140° C. until a constant reactor pressure is obtained, and the product is then cooled down.

The product contains 201 ppm of an ultra-high molecular weight polymer, as measured by GPC using Waters 2690/5 Separations Module and 410 RI Detector in combination with the Empower Pro Software. The column is a PL-gel column (30 cm×0.7 internal diameter) filled 5 micron PS/DVB copolymer particles having a pore size of 1000 angstroms. The eluent is tetrahydrofuran, at a flow rate of 1 mL/minute. The detector temperature is 35° C., the peak width is greater than 0.2 min, attenuation is 62,500 nRIU, 1 V output and 12 minutes run time. The GPC system was calibrated using narrow polystyrene standards EasiCal PS-1 A/B and a polystyrene 100 kDa narrow standard diluted in THF to concentrations in the range from 180 to 1.8 mg PS/L. HMWT as reported here is the fraction of the distribution whose molecular weight is higher than 40,000 g/mol.

EXAMPLE 32

Example 31 is repeated, substituting an equal amount of titanium isopropoxide for the hafnium tetra(tert-butoxide). The product contains 784 ppm of the ultra-high molecular weight tail.

Comparative Run R is performed in the same way, but no hafnium or titanium compound is present. The catalyst activates more slowly, and performs sluggishly at the end of the propylene oxide feed. The product contains 1196 ppm of the ultra-high molecular weight tail.

EXAMPLE 33, 34, 35 AND COMPARATIVE RUN S

Example 33: Into the shell of a 500 mL Autoclave Engineers reactor are placed 45 g of a propoxylate of glycerin that has an average molecular weight of 450 (Voranol® CP450, The Dow Chemical Company). 1.7 microliters of a 0.15 M phosphoric acid solution in water, and 0.0030 g of the Arcol 3 catalyst. 0.037 mole of Aluminum isopropoxide/gram of DMC catalyst complex (enough to provide 10 parts per million of aluminum based on the expected mass of the product) is added and stirred in. The shell of the reactor is then placed on the reactor frame, and the reaction mixture is stirred and heated at a temperature of 145° C. for 90 minutes with a slow purge of nitrogen (0.5 standard cubic feet (14 liters) per hour) passing through the reactor contents. The reactor contents are heated to 150° C., and, while maintaining that temperature, propylene oxide (PO) is introduced into the reactor at a rate of 1.0 mL/min. The reactor initially climbs to an internal reactor pressure of 16.8 psig (116 kPa), at which time the pressure begins to decline slowly to a pressure of 6.2 psig (43 kPa) with a constant feed of PO at 1.0 mL/min. There is no pause in PO feed for catalyst activation. Eventually the pressure in the reactor begins to rise due to the compression of nitrogen gas in the reactor. The feed is continued until a total of 309.1 mL (255.0 g) of PO has been fed into the reactor. The time required to complete the PO feed is 5 hrs and 24 minutes. After all the PO has been fed into the reactor, the reaction mixture is cooked down at 150° C. until a steady internal reactor pressure (indicative of complete polymerization of the charged PO) is achieved. The PO digest time for this reaction is 12 minutes. A 3000 number average molecular weight product is obtained. The final DMC catalyst concentration in the reactor is 10 ppm.

Example 34 is performed in the same general manner as Example 33, except the amount of the DMC catalyst complex is reduced by 50% (to a final concentration of 5 ppm. The time to catalyst activation is 12 minutes. The time required to complete the PO feed is 3 hrs and 55 minutes. The PO digest time for this reaction is 18 minutes. A 3000 number average molecular weight product is obtained.

Example 35 is performed in the same general manner as Example 33, except the amount of the DMC catalyst complex is reduced to 2.5 ppm, based on the weight of the final product, and the amount of aluminum isopropoxide is only 0.0008 g (0.037 mole of aluminum per gram of DMC catalyst complex. The time to catalyst activation is 32 minutes. The time required to complete the PO feed is 6 hrs and 12 minutes. The PO digest time for this reaction is 49 minutes. A 3000 number average molecular weight product is obtained.

In comparative run S, the same recipe is used as in Example 33, except that the aluminum isopropoxide is left out of the reaction mixture. In this case, upon initial PO feed, the reactor internal pressure climbs to 20 psig (138 kPa), at which time the PO feed is stopped and the reactor is closed to wait for catalyst activation. After 2 hours the reactor pressure has declined to 10 psig (69 kPa), indicating catalyst activation. The PO feed is re-started, but the reactor pressure quickly climbs to 20 psig (138 kPa) again. The feed rate of PO is maintained at less than 0.5 ml/minute in order to maintain an internal reactor pressure of 20 psig (138 kPa). After a total feed time of over 16 hours the reaction is abandoned due to poor catalyst activity.

Examples 33, 34 and 35 illustrate that the addition of aluminum isopropoxide to the reaction mixture enables the use of substantially less DMC catalyst for the preparation of high molecular weight polyether polyols than can be used without the addition of aluminum isopropoxide.

EXAMPLES 36-39 AND COMPARATIVE RUN T

Into the shell of a 500 mL Autoclave Engineers reactor are placed 33.6 g of tripropylene glycol (a molecular weight of 192) (The Dow Chemical Company), 1.3 microliters of 0.15M $H_3PO_4$, 0.0088 g of the Arcol 3 catalyst, and 0.037 mole of Aluminum isopropoxide/gram of DMC catalyst complex (enough to provide 25 parts per million of aluminum based on the expected mass of the final product) is added and stirred in. The shell of the reactor is then placed on the reactor frame, and the reaction mixture is stirred and heated at a temperature of 120° C. for 120 minutes with a slow purge of nitrogen (0.5 standard cubic feet (14 liters) per hour) passing through the reactor contents. The reactor contents are heated to 150° C., and, while maintaining that temperature, propylene oxide (PO) is introduced into the reactor at a rate of 1.0 mL/min. The reactor initially climbs to an internal reactor pressure of 20.0 psig (138 kPa), at which time the PO feed is stopped and the reactor is closed. The internal pressure begins to decline slowly to a pressure of 10.0 psig (69.0 kPa), at which point the PO feed is resumed. The time to catalyst activation is 35.5 minutes. The PO feed rate is controlled to maintain an internal reactor pressure of 25.0 psig±1.0 psig. Eventually the pressure in the reactor begins to rise due to the compression of nitrogen gas in the reactor. The feed is continued at a rate as high as 2.5 mL/minute until a total of 383.9 mL (316.4 g) of PO has been fed into the reactor. The time required to complete the PO feed is 3 hrs and 46 minutes. After all the PO has been fed into the reactor, the reaction mixture is cooked down at 150° C. until a steady internal reactor pressure (indicative of complete polymerization of the charged PO) is achieved. The PO digest time for this reaction is 12 minutes. A ~2000 number average molecular weight product is obtained. The final DMC catalyst concentration in the reactor is 75 ppm.

Comparative run T is performed in the same manner as Example 36, except the aluminum isopropoxide is not included in the reaction mixture. The time to catalyst activation is 32 minutes. Upon resumption of the PO feed, the feed rate is very slow, no more than 0.25 ml/minute, and after 70 minutes the reaction is abandoned due to low catalyst activity.

Examples 37-39 are run under similar conditions as Example 36. Example 39 is run at a lower maximum feed rate of PO (1.5 ml/min) to demonstrate that lowering the feed rate results in a lower polydispersity in the final product, compared to the same catalyst loading run at a higher feed rate (Example 38). Results are as indicated in Table 2.

TABLE 2

| Designation | Catalyst | Activation Time | Batch Time (h:m) | $M_n$ | $M_w$ | PDI |
|---|---|---|---|---|---|---|
| T | 25 ppm DMC 0 ppm Al | 0:32:00 | — | 249 | 256 | 1.028 |
| 36 | 25 ppm DMC 25 ppm Al (i-OPr)$_3$ | 0:24:30 | 3:40 | 2116 | 2154 | 1.018 |
| 37 | 12.5 ppm DMC 12.5 ppm Al (i-OPr)$_3$ | 0:18:00 | 3:28 | 2091 | 2136 | 1.022 |
| 38 | 6 ppm DMC 6 ppm Al (i-OPr)$_3$ | 0:22:00 | 4:45 | 2098 | 2247 | 1.071 |
| 39 | 6 ppm DMC 6 ppm Al (i-OPr)$_3$ | 0:39:30 | 7:16 | 2098 | 2186 | 1.042 |

Under these conditions, the DMC catalyst complex when used by itself activates after 32 minutes but rapidly deactivates and only produces a low molecular weight oligomer. When aluminum isopropoxide is added into the catalyst mixture, the polymerization proceeds rapidly to produce a ~2000 molecular weight product. Examples 37 and 38 show that DMC catalyst levels can be reduced to as low as 6 ppm under these conditions while still achieving a shorter activation time than the control and rapid polymerization to the desired molecular weight. A longer polymerization time is seen in Example 39 due to the lower PO feed rate, but the target molecular weight is easily achieved with the benefit of lower polydispersity.

EXAMPLES 40-48 AND COMPARATIVE RUNS U-X

Example 40: Into the shell of a 500 mL Autoclave Engineers reactor are placed 96 g of tripropylene glycol (a molecular weight of 192) (The Dow Chemical Company), and 0.015 g of the Arcol 3 catalyst. 0.037 mole of Aluminum isopropoxide/gram of DMC catalyst complex (enough to provide 75 parts per million of aluminum based on the expected mass of the product) is added and stirred in. The shell of the reactor is then placed on the reactor frame, and the reaction mixture is stirred and heated at a temperature of 120° C. for 90 minutes with a slow purge of nitrogen (0.5 standard cubic feet (14 liters) per hour) passing through the reactor contents. The reactor contents are heated to 150° C., and, while maintaining that temperature, propylene oxide (PO) is introduced into the reactor at a rate of 1.0 mL/min. The reactor initially climbs to an internal reactor pressure of 20.0 psig (138 kPa), at which time the PO feed is stopped and the reactor is closed. The internal pressure begins to decline slowly to a pressure of 10.0 psig (69.0 kPa), at which point the PO feed is resumed. The time to catalyst activation is 29 minutes. The PO feed rate is controlled to maintain an internal reactor pressure of 20.0 psig±1.0 psig. Eventually the pressure in the reactor begins to rise due to the compression of nitrogen gas in the reactor. The feed is continued at a rate as high as 3.0 ml/minute until a total of 126.1 mL (104.0 g) of PO has been fed into the reactor. The time required to complete the PO feed is 3 hrs and 25 minutes. After all of the PO has been fed into the reactor, the reaction mixture is cooked down at 150° C. until a steady internal reactor pressure (indicative of complete polymerization of the charged PO) is achieved. The PO digest time for this reaction is 10 minutes. A 400 number average molecular weight product is obtained. The final DMC catalyst concentration in the reactor is 75 ppm.

Comparative run U is performed in the same general manner as Example 40, except the aluminum isopropoxide is not included in the reaction mixture. The time to catalyst activation is 64 minutes. Upon resumption of the PO feed, the feed rate is very slow, less than 0.1 ml/minute, and after 90 minutes the reaction is abandoned due to low catalyst activity.

Examples 41 through 48 are run in an identical fashion as Example 40, except that different aluminum compounds replace the aluminum isopropoxide. In all cases 0.037 mole of metal complex is added to the reaction mixture. Results are as indicated in Table 3.

TABLE 3

| Designation | Metal Compound | Activation time (h:m) | PO Feed time (h:m) |
|---|---|---|---|
| U | None | 1:04 | abandoned |
| 40 | Aluminum Isopropoxide | 0:29 | 3:25 |
| 41 | methyl aluminoxane | 0:34 | 3:21 |
| 42 | Aluminum Phenoxide | 0:30 | 1:41 |
| 43 | Aluminum 4-cyanophenoxide | 1:21 | 3:35 |
| 44 | Aluminum 4-methoxyphenoxide | 0:26 | 1:43 |
| 45 | Aluminum Benzoate | 0:56 | 3:28 |
| 46 | Aluminum 4-cyanobenzoate | 1:20 | 4:42 |
| 47 | Aluminum 4-trifluoromethylbenzoate | 1:16 | 5:34 |
| 48 | Aluminum 4-methoxybenzoate | 0:47 | 3:28 |
| V | Aluminum Sulfate | No activation | abandoned |
| W | Aluminum Triflate | 0:00 | abandoned |
| X | Aluminum Iodide | 1:08 | abandoned |

These samples represent rather stringent conditions for a DMC catalyst complex because of the low molecular weight of the product and the correspondingly high concentration of hydroxyl groups. The DMC catalyst by itself (Comparative Sample U) activates under these conditions but rapidly deactivates and does not produce the desired 400 molecular weight product. As can be seen from Table 3, a range of aluminum alkoxides, phenoxides and benzoate compounds Examples 40-48) permit the polymerization to proceed to the desired molecular weight. Aluminum salts of strong inorganic acids (sulfate and iodide) do not produce the desired 400 molecular weight product; in the case of aluminum sulfate the DMC catalyst fails to activate at all. Aluminum triflate exhibits characteristics of strong Lewis acid catalysis. The polymerization begins immediately, but discontinues very rapidly and only very low molecular weight products are obtained. In this sample, there is no evidence that the DMC catalyst becomes activated.

EXAMPLE 49

Into the shell of a 500 mL Autoclave Engineers reactor are placed 33.6 g of tripropylene glycol (a molecular weight of 192) (The Dow Chemical Company), 0.0088 g of the Arcol 3 catalyst, and 0.066 g of aluminum isopropoxide. No phosphoric acid is added to this reaction mixture. No pre-drying step is performed on this reaction mixture. The shell of the reactor is then placed on the reactor frame, and the reaction mixture is heated to 150° C., and, while maintaining that temperature, propylene oxide (PO) is introduced into the reactor at a rate of 1.0 mL/min. The reactor initially climbs to an internal reactor pressure of 20.0 psig (138 kPa), at which time the PO feed is stopped and the reactor is closed. The internal pressure declines slowly to a pressure of 10.0 psig (69.0 kPa), at which point the PO feed is resumed. The time to catalyst activation is 36 minutes. The feed is continued at a rate as high as 3.0 ml/minute until a total of 383.5 mL (316.4 g) of PO has been fed into the reactor to produce a 2000 MW diol. The time required to complete the PO feed is 5 hrs and 30 minutes. After all the PO has been fed into the reactor, the reaction mixture is cooked down at 150° C. until a steady internal reactor pressure (indicative of complete polymerization of the charged PO) is achieved. The PO digest time for this cook down step is 10 minutes. A 2000 number average molecular weight product is obtained. The final DMC catalyst concentration in the reactor is 25 ppm.

COMPARATIVE RUN Y

Comparative run Y is performed in the same manner as Example 49, except the aluminum isopropoxide is not included in the reaction mixture. The time to catalyst activation is greater than 3 hours. Upon resumption of the PO feed, the feed rate is very slow, less than 0.1 ml/minute, and after 35 minutes the reaction is abandoned due to low catalyst activity.

EXAMPLES 50-65 AND COMPARATIVE SAMPLE Z

Tripropylene glycol (120 g), DMC catalyst (0.012 g), and $H_3PO_4$ (6 uL), and the metal compound ($4.5 \times 10^{-4}$ mole) are blended, and this mixture is loaded into a 600 ml stainless steel Parr reactor which is at a temperature of 70° C. This mixture is sparged with nitrogen while stirring at 300 rpm for 2 hours. The temp is then increased to 150° C. and agitator is increased to 700 rpm. After venting excess pressure, PO is fed at a rate of 0.7 mL/min. The feed is continued in this way until either A) 12 mL of PO is added or B) the pressure reaches 20 psi. If A, then the catalyst is considered activated, and the maximum reactor pressure recorded during this initial PO feed is recorded. In case A, the feed is stopped for 30 seconds to observe a short digestion window, then the feed is restarted at 1.5 mL/min until a total of 130 ml (156 g) of PO is fed to the reactor. If B, the feed is stopped, the digestion of the added PO is followed until the reactor reaches an internal pressure of about 10 psi, then the feed is restarted at 0.7 mL/min until a total of 12 mL of PO is fed to the reactor. At this point the feed is stopped for 30 seconds to observe a short digestion window, then the feed is restarted at 1.5 mL/min until a total of 130 ml (156 g) of PO is fed to the reactor. A 400 MW diol product is produced from the reaction, containing a final DMC catalyst concentration of 50 ppm.

Comparative Sample Z represents the average of six runs performed in the same manner, except no MG3-15LA compound is present.

TABLE 4

| Designation | Compound | Activation Pressure (psig) |
|---|---|---|
| Z | None | 18.9 |
| 50 | Aluminum 2-butoxide | 13.4 |
| 51 | Aluminum acetoacetonate | 13.3 |
| 52 | Bismuth triphenyl | 10.8 |
| 53 | Gallium dimethylamide | 9.8 |
| 54 | Gallium acetylacetonate | 10.9 |
| 55 | Hafnium isopropoxide | 11.6 |
| 56 | Indium acetylacetonate | 12.5 |
| 57 | Indium acetate | 17.1 |
| 58 | Niobium ethoxide | 11.7 |
| 59 | Scandium isopropoxide | 8.6 |
| 60 | Titanium isopropoxide | 12 |
| 61 | Vanadium tris(acetoacetonate) | 15.3 |
| 62 | Yttrium 2-ethylhexanoate | 12.4 |
| 63 | Yttrium (N(SiMe3)2)3 | 10 |
| 64 | Yttrium (t-Bu acac)3 | 8.4 |
| 65 | Yttrium Oxo [OiPr]13 | 13.1 |

The catalyst activates more rapidly in each of Examples 50-65 than in Comparative Sample Z, under the stringent conditions of this test.

EXAMPLES 66-78 AND COMPARATIVE RUN AA

Tripropylene glycol (120 g), DMC catalyst (0.018 g), and a MG3-15LA compound ($1.5 \times 10^{-4}$ mole) are blended, and 100 g of this mixture is loaded into a 600 ml stainless steel Parr reactor which is at a temperature of 70° C. This mixture is sparged with nitrogen at 120° C. while stirring at 300 rpm for 40 minutes. The temperature is then increased to 150° C. and agitator is increased to 700 rpm. After venting excess pressure, PO is fed at a rate of 1.0 mL/min. The feed is continued in this way until the pressure reaches 20 psig. The feed is stopped, and the digestion of the added PO is followed until the reactor reaches an internal pressure of 10 psig. The time required to digest the reactor pressure from 20 psig to 10 psig is recorded as the activation time. In some cases the catalyst activity is so high that the reactor never reaches an initial pressure of 20 psig, in that case the PO feed is stopped after the addition of 12 ml of PO and the time required to reach 10 psig is recorded as the activation time. The PO feed is restarted and is controlled at a rate that maintains an internal reactor pressure of 20 psig±1 psig until a total of 130 ml (109 g) of PO is fed to the reactor. In cases in which the catalyst activated and the polymerization was completed, a 400 MW diol product is produced, containing a final DMC catalyst concentration of 75 ppm.

TABLE 5

| Designation | MG3-15LA Compound | Activation time (h:m) | PO Feed time (h:m) |
|---|---|---|---|
| AA* | None | 0:59 | Discontinued |
| 66 | Zirconium(isopropoxide)$_4$•isopropanol | 0:15 | 1:35 |
| 67 | Yttrium (t-butylacetoacetonate(3 | 0:13 | 1:12 |
| 68 | Aluminum sec-butoxide | 0:37 | 4:45 |
| 69 | Gallium tris(dimethylamide) | 0:15-0:29 | 1:15-2:45[2] |
| 70 | Titanium tetra(isopropoxide) | 0:36 | Discontinued[1] |
| 71 | Niobium penta(ethoxide) | 0:24 | Discontinued[1] |
| 72 | Chromium tris(acetylacetonate) | 0:21 | 3:40 |
| 73 | Manganese bis(acetoacetonate) | 0:36 | Discontinued[1] |
| 74 | Copper bis(acetoacetonate) | 0:45 | 3:30 |
| 75 | Vanadium tris(acetoacetonate) | 0:11 | Discontinued[1] |
| 76 | Lanthanum tris[(dimethylsilyl)amide] | 0:15 | 10:05 |
| 77 | Ytterbium tris[dimethylsilyl)amide] | 0:08 | 1:12 |
| 78 | Gallium tris(dimethylamide) and zirconium tetra (isopropoxide) | 0:15 | 1:15 |

*Not an example of this invention.
[1]These runs are discontinued before the polymerization all of the propylene oxide is fed. The rate of reaction in these examples prior to the discontinuation of the propylene oxide is in all cases about 2-5 times that of Comparative Sample AA.

Once again, this test represents stringent polymerization conditions under which the DMC catalyst by itself is difficult to activate. The MG3-15LA compounds of Examples 66-78 all reduce the activation time and increase the polymerization rate, in many cases very substantially, compared to the DMC catalyst complex by itself.

EXAMPLES 79 AND 80 AND COMPARATIVE RUN AB

Comparative Run AB: Into a 5 L stainless steel autoclave reactor are placed 493 g of a phenol formaldehyde oligomeric condensate with average functionality 3.4 and $M_n$ of 350 g/mol, 2 drops of a 85% phosphoric acid solution in water, and 0.3416 g of a DMC catalyst. The reaction mixture is stripped in vacuum with stirring at a temperature of 100° C. for 60 minutes. The reactor is then sealed with nitrogen without breaking the vacuum. The reactor contents are heated to 150° C., and, while maintaining that temperature, 60 g propylene oxide (PO) is introduced into the reactor to produce an internal reactor pressure of 215 kPa actual, at which time the reactor is sealed. The pressure inside the reactor is monitored. The internal reaction pressure declines to about 110 kPa actual in 16 minutes. Still maintaining a temperature of 150° C., a PO feed is introduced into the reactor, at a rate sufficient to maintain an internal reactor pressure of 560 kPa actual. This feed is continued for 140 minutes until a total of 484 g of PO (including the initial PO charge) has been fed into the reactor. At this point, a sudden drop in pressure, accompanied by an exotherm, is observed. Another 389 g of PO is then fed within 30 minutes at an average feed rate of 13 g/min. After all the PO has been fed into the reactor, the reaction mixture is cooked down at 150° C. A steady internal reactor pressure (indicative of complete polymerization of the charged PO) is achieved after 25 minutes.

The resulting polyether polyol product has the following properties: OH value: 197 mg KOH/g; water: 50 ppm; viscosity at 50° C.: 4530 cSt; $M_n$ (by GPC): 786 g/mol, $M_w/M_n$=1.49. The product contains about 84% secondary hydroxyl groups, 14% primary hydroxyl groups and 1% phenolic hydroxyl groups Example 79 is performed in the same manner, except this time 3.11 g of aluminum tri-sec-butoxide (0.037 moles/g of DMC catalyst complex) is added to the reactor after the DMC catalyst is added and thoroughly mixed into the reaction mixture. In this case, the digestion of the first portion of 60 g PO requires only 13 minutes, and the remaining 813 g PO feed requires only 56 minutes. After addition of all the propylene oxide, a steady internal reaction pressure is achieved after 90 minutes The product of Example 79 has a hydroxyl number of 183, a water content of 90 ppm; a viscosity at 50° C. of 8370 mPa·s; $M_n$ (by GPC) of 814 g/mol, and a $M_w/M_n$ of 1.48. The product contains about 58% secondary hydroxyl groups, 37% primary hydroxyl groups and 5% phenolic hydroxyl groups.

Example 80 is performed in the same manner as the Example 79, except this time the starter is extensively dried four 4 hours at 130° C. by applying a nitrogen sparge from the bottom of the reactor and a vacuum from the top of it, such that the total pressure inside the reactor is kept at 10 mbar. The residual level of water in the starter is below 200 ppm. 4.98 g of aluminum tri-sec-butoxide (0.037 moles/g of DMC catalyst complex) is added to the reactor after 0.55 g of the DMC catalyst has been added, and thoroughly is mixed into the reaction mixture. The digestion of the first 80 g of PO requires only 5 minutes, and the remaining 1320 g PO feed requires 87 minutes. A steady internal reaction pressure is thereafter achieved after cooking the reaction mixture down for 70 minutes.

The product of Example 80 has a hydroxyl number of 171, a water content of 90 ppm, a viscosity at 50° C. of 5860 mPa·s; an $M_n$ (by GPC) of 785 g/mol, and an $M_w/M_n$=1.55. The product contains 49% secondary hydroxyl groups, 36% primary hydroxyl groups and 15% phenolic hydroxyl groups.

EXAMPLE 81 AND COMPARATIVE RUN AC

Example 81: A 700 molecular weight poly(propylene oxide) triol (Voranol® 270, The Dow Chemical Company) (120 g), DMC catalyst (0.022 g), and 1.0 g of 1.0 M MgBu$_2$ in hexanes are combined and blended, and 100 g of this mixture is loaded into a 600 ml stainless steel Parr reactor which is at a temperature of 70° C. This mixture is sparged with nitrogen while stirring at 300 rpm for 2 hours. The temperature is then increased to 150° C. and agitator is increased to 1000 rpm. After venting excess pressure, PO is fed at a rate of 0.7 mL/min until 10 mL of PO is added, and the highest pressure attained (activation pressure) is 6.9 psig (47 kPa). The feed is stopped after 10 mL of PO is added to allow digestion to a constant pressure. The PO feed is restarted at 1.5 mL/min and maintained until a total of 380 ml (315 g) of PO is fed to the reactor. After digestion, a 3000 MW triol product is produced from the reaction, containing a final DMC catalyst concentration of 55 ppm. The final product contains 356 ppm of a high (>40,000 g/mol) molecular weight fraction.

When example 81 is repeated (Comparative Run AC) without MgBu$_2$ present, the activation pressure is 13.3 psig and the final product contains 979 ppm of the high molecular weight fraction.

What is claimed is:

1. A method for producing a polyether monol or polyether polyol product, comprising polymerizing at least one alkylene oxide in the presence of a double metal cyanide catalyst complex and at least one magnesium, gallium or indium compound not present during the preparation of the double metal cyanide catalyst complex in which magnesium, gallium or indium is bonded to at least one alkoxide, aryloxy, carboxylate, acyl, pyrophosphate, phosphate, thiophosphate, dithiophosphate, phosphate ester, thiophosphate ester, amide, siloxide, hydride, carbamate or hydrocarbon anion, and wherein the magnesium, gallium or indium compound is devoid of halide anions.

2. The method of claim 1 which includes the steps of:
combining (a) the double metal cyanide catalyst complex (b) the magnesium, gallium or indium compound, (c) at least one initiator compound, and (d) at least one alkylene oxide to form a starting reaction mixture,
heating the starting reaction mixture to polymerization conditions until the double metal cyanide catalyst complex becomes activated, and then
feeding additional alkylene oxide to the reaction mixture under polymerization conditions.

3. The method of claim 1 which includes the steps of:
establishing steady-state concentrations of 1) the DMC catalyst, 2) the magnesium, gallium or indium compound, 3) at least one initiator, 4) at least one alkylene oxide and 5) polymerizate in a continuous reactor under polymerization conditions,
continuously adding additional initiator, alkylene oxide, DMC catalyst complex, additional magnesium, gallium or indium compound, or a catalyst mixture formed by combining the DMC catalyst complex and magnesium, gallium or indium compound, to the continuous reactor under polymerization conditions and continuously withdrawing a product stream containing polyether monol or polyether polyol product from the continuous reactor.

4. A method for preparing an alkylene oxide polymerization catalyst mixture, comprising combining (a) a double metal cyanide catalyst complex and (b) at least one magnesium, gallium or indium compound not present during the preparation of the double metal cyanide catalyst complex in which magnesium, gallium or indium is bonded to at least one alkoxide, aryloxy, carboxylate, acyl, pyrophosphate, phosphate, thiophosphate, dithiophosp hate, phosphate ester, thiophosp hate ester, amide, siloxide, hydride, carbamate or hydrocarbon anion, and wherein the magnesium, gallium or indium compound is devoid of halide anions to form a catalyst mixture and then performing a preliminary heating step by heating the catalyst mixture to a temperature of from 80 to 220° C. at atmospheric or subatmospheric pressure for a period of 10 minutes or more prior to combining the catalyst mixture with an alkylene oxide.

5. The method of claim 1, wherein the magnesium, gallium or indium compound is one or more of a trialkyl gallium compound; a gallium alkoxide; a gallium aryloxide; a gallium carboxylate, a gallium amide; gallium acetylacetonate; gallium t-butylacetylacetonate; an alkylgallium alkoxide; a trialkyl indium compound; an indium aryloxide; an indium carboxylate; indium acetylacetonate; and indium t-butylacetylacetonate.

6. The method of claim 1, wherein the magnesium, gallium or indium compound is one or more of trimethylgallium, triethyl gallium, tributyl gallium, tribenzylgallium, trimethoxide, gallium triethoxide, gallium triisopropoxide, gallium tri-t-butoxide, gallium tri-sec-butoxide, gallium phenoxide, a gallium phenoxide in which one or more of the phenoxide groups is ring-substituted with alkyl, CF$_3$, cyano, COCH$_3$, halogen, hydroxyl or alkoxyl, gallium formate, gallium acetate, gallium propionate, gallium 2-ethylhexanoate, gallium benzoate, a gallium benzoats in which one or more of the benzoate groups is ring-substituted with alkyl, CF$_3$, cyano, COCH$_3$, halogen, hydroxyl or alkoxyl, gallium salicylate, gallium 3,5-di-t-butyl salicylate; gallium tris(dimethylamide), gallium tris(diethylamide), gallium tris(dip henylamide), gallium tris(di(trimethylsilyl)amide), gallium acetylacetonate, gallium t-butylacetylacetonate, diethylgallium ethoxide, dimethylgallium ethoxide, diethylgallium isopropoxide, dimethylgallium isopropoxide, trimethyl indium, indium methoxide, indium ethoxide, indium isopropoxide, indium t-butoxide, indium sec-butoxide, indium phenoxide, and indium phenoxide in which one or more of the phenoxide groups is ring-substituted with alkyl, CF$_3$, cyano, COCH$_3$, halogen, hydroxyl or alkoxyl; indium formate, indium acetate, indium propionate, indium 2-ethylhexanoate, indium benzoate, an indium benzoate in which one or more of the benzoate groups is ring-substituted with alkyl, CF$_3$, cyano, COCH$_3$, halogen, hydroxyl or alkoxyl, indium salicylate, indium 3,5-di-t-butyl salicylate, indium acetylacetonate and indium t-butylacetylacetonate.

7. The method of claim 1 wherein the magnesium, gallium or indium compound is a gallium or indium alkoxide, wherein at least one alkoxide group of the gallium or indium alkoxide is a residue, after removal of at least one hydroxyl hydrogen, of a polyether monol or polyether polyol.

8. The method of claim 4, wherein the magnesium, gallium or indium compound is one or more of a trialkyl gallium compound; a gallium alkoxide; a gallium aryloxide; a gallium carboxylate, a gallium amide; gallium acetylacetonate; gallium t-butylacetylacetonate; an alkylgallium alkoxide; a trialkyl indium compound; an indium aryloxide; an indium carboxylate; indium acetylacetonate; and indium t-butylacetylacetonate.

9. The method of claim 4, wherein the magnesium, gallium or indium compound is one or more of trimethylgallium, triethyl gallium, tributyl gallium, tribenzylgallium, trimethoxide, gallium triethoxide, gallium triisopropoxide, gallium tri-t-butoxide, gallium tri-sec-butoxide, gallium phenoxide, a gallium phenoxide in which one or more of the phenoxide groups is ring-substituted with alkyl, CF$_3$, cyano, COCH$_3$, halogen, hydroxyl or alkoxyl, gallium formate, gallium acetate, gallium propionate, gallium 2-ethylhexanoate, gallium benzoate, a gallium benzoats in which one or more of the benzoate groups is ring-substituted with alkyl, CF$_3$, cyano, COCH$_3$, halogen, hydroxyl or alkoxyl, gallium salicylate, gallium 3,5-di-t-butyl salicylate; gallium tris(dimethylamide), gallium tris(diethylamide), gallium tris(diphenylamide), gallium tris(di(trimethylsilyl)amide), gallium acetylacetonate, gallium t-butylacetylacetonate, diethylgallium ethoxide, dimethylgallium ethoxide, diethylgallium isopropoxide, dimethylgallium isopropoxide, trimethyl indium, indium methoxide, indium ethoxide, indium isopropoxide, indium t-butoxide, indium sec-butoxide, indium phenoxide, and indium phenoxide in which one or more of the phenoxide groups is ring-substituted with alkyl, CF$_3$, cyano, COCH$_3$, halogen, hydroxyl or alkoxyl; indium formate, indium acetate, indium propionate, indium 2-ethylhexanoate, indium benzoate, an indium benzoate in which one or more of the benzoate groups is ring-substituted with alkyl, CF$_3$, cyano, COCH$_3$, halogen, hydroxyl or alkoxyl, indium salicylate, indium 3,5-di-t-butyl salicylate, indium acetylacetonate and indium t-butylacetylacetonate.

10. The method of claim 1, wherein the magnesium, gallium or indium compound is one or more of a magnesium alkyl, a magnesium alkoxide, a magnesium aryloxide, a magnesium carboxylate, a magnesium amide, a magnesium acetylacetonate and magnesium t-butylacetylacetonate.

11. The method of claim 1, wherein the magnesium, gallium or indium compound is one or more of diethyl magnesium, dibutyl magnesium, butylethyl magnesium, dibenzyl magnesium, magnesium methoxide, magnesium ethoxide, magnesium isopropoxide, magnesium t-butoxide, magnesium sec-butoxide, magnesium phenoxide, a magnesium phenoxide in which one or more of the phenoxide groups is ring-substituted with alkyl, CF$_3$, cyano, COCH$_3$, halogen, hydroxyl or alkoxyl; magnesium formate, magnesium acetate, magnesium propionate, magnesium 2-ethylhexanoate, magnesium benzoate, a magnesium benzoate in which one or more of the benzoate groups is ring-substituted with alkyl, CF$_3$, cyano, COCH$_3$, halogen, hydroxyl or alkoxyl, magnesium salicylate, magnesium 3,5-di-t-butyl salicylate, magnesium dimethylamide, magnesium diethylamide, magnesium diphenylamide, magnesium bis(trimethylsilyl)amide, magnesium acetylacetonate and magnesium t-butylacetylacetonate.

12. The method of claim 1 wherein the magnesium, gallium or indium compound is a magnesium alkoxide, wherein at least one alkoxide group of the magnesium alkoxide is a residue, after removal of at least one hydroxyl hydrogen, of a polyether monol or polyether polyol.

13. The method of claim 1, wherein the magnesium, gallium or indium compound is a magnesium compound which is present in an amount sufficient to provide 0.0025 to 0.5 moles of magnesium per gram of the double metal cyanide catalyst complex.

14. The method of claim 4, wherein the magnesium, gallium or indium compound is one or more of a magnesium alkyl, a magnesium alkoxide, a magnesium aryloxide, a magnesium carboxylate, a magnesium amide, a magnesium acetylacetonate and magnesium t-butylacetylacetonate.

15. The method of claim 4, wherein the magnesium, gallium or indium compound is one or more of diethyl magnesium, dibutyl magnesium, butylethyl magnesium, dibenzyl magnesium, magnesium methoxide, magnesium ethoxide, magnesium isopropoxide, magnesium t-butoxide, magnesium sec-butoxide, magnesium phenoxide, a magnesium phenoxide in which one or more of the phenoxide groups is ring-substituted with alkyl, CF$_3$, cyano, COCH$_3$, halogen, hydroxyl or alkoxyl; magnesium formate, magnesium acetate, magnesium propionate, magnesium 2-ethylhexanoate, magnesium benzoate, a magnesium benzoate in which one or more of the benzoate groups is ring-substituted with alkyl, CF$_3$, cyano, COCH$_3$, halogen, hydroxyl or alkoxyl, magnesium salicylate, magnesium 3,5-di-t-butyl salicylate, magnesium dimethylamide, magnesium diethylamide, magnesium diphenylamide, magnesium bis(trimethylsilyl)amide, magnesium acetylacetonate and magnesium t-butylacetylacetonate.

\* \* \* \* \*